United States Patent [19]
Kensey et al.

[11] Patent Number: 5,545,178
[45] Date of Patent: Aug. 13, 1996

[54] SYSTEM FOR CLOSING A PERCUTANEOUS PUNCTURE FORMED BY A TROCAR TO PREVENT TISSUE AT THE PUNCTURE FROM HERNIATING

[75] Inventors: Kenneth Kensey, Chester Springs; John E. Nash, Downington; Douglas Evans, Devon, all of Pa.

[73] Assignee: Kensey Nash Corporation, Exton, Pa.

[21] Appl. No.: 327,262

[22] Filed: Oct. 21, 1994

Related U.S. Application Data

[63] Continuation-in-part of Ser. No. 235,825, Apr. 29, 1994.

[51] Int. Cl.$^6$ .................................................. A61B 17/04
[52] U.S. Cl. ............................... 606/213; 604/15; 604/60; 606/232
[58] Field of Search ............................. 606/139, 213, 606/215, 216, 228–232; 604/15

[56] References Cited

U.S. PATENT DOCUMENTS

| | | | |
|---|---|---|---|
| 4,890,612 | 1/1990 | Kensey et al. | 606/213 |
| 4,946,468 | 8/1990 | Li | 606/232 |
| 5,021,059 | 6/1991 | Kensey et al. | 606/252 |
| 5,053,096 | 10/1991 | Janese | 606/215 |
| 5,092,884 | 3/1992 | Devereux et al. | |
| 5,116,357 | 5/1992 | Eberbach . | |
| 5,141,515 | 8/1992 | Eberbach . | |
| 5,220,928 | 6/1993 | Oddsen et al. | |
| 5,222,435 | 6/1993 | Kensey et al. | 606/213 |
| 5,222,974 | 6/1993 | Kensey et al. | 606/213 |
| 5,254,133 | 10/1993 | Seid . | |
| 5,274,074 | 12/1993 | Tang et al. . | |
| 5,282,827 | 2/1994 | Kensey et al. | 606/215 |
| 5,290,217 | 3/1994 | Campos . | |
| 5,312,435 | 5/1994 | Nash et al. | 606/213 |
| 5,312,794 | 5/1994 | Nash et al. | 606/213 |
| 5,342,393 | 8/1994 | Stack | 606/215 |
| 5,417,699 | 5/1995 | Klein et al. | 606/252 |

FOREIGN PATENT DOCUMENTS

| | | |
|---|---|---|
| WOA8911301 | 11/1989 | WIPO . |
| WOA9308746 | 5/1993 | WIPO . |
| WO94/13211 | 6/1994 | WIPO . |

Primary Examiner—Gary Jackson
Attorney, Agent, or Firm—Caesar, Rivise, Bernstein, Cohen & Pokotilow, Ltd.

[57] ABSTRACT

A system and method for sealing a percutaneous puncture extending into internally located tissue, e.g., the peritoneum, of a living being. The system includes a sealing device and a deployment instrument. In one embodiment the sealing device comprises a substantially rigid anchor, a resorbable holding member, a collagen plug, and a resorbable thin filament connecting the anchor, holding member, and plug. The anchor or the plug or both may be formed of a resorbable material having a non-resorbable mesh reinforcement embedded therein. The deployment instrument is operated to place the anchor in the interior of the peritoneum and the plug and the holding member in the puncture tract, with both ends of the filament extending out of the puncture. The extending ends of the filament are formed into a knot, a portion of which extends through the skin contiguous with the puncture, to lock the closure in place. The reinforced mesh of the closure reinforces any scar tissue which forms at the opening. In an alternative embodiment the sealing device comprises only the anchoring member and the filament.

75 Claims, 16 Drawing Sheets

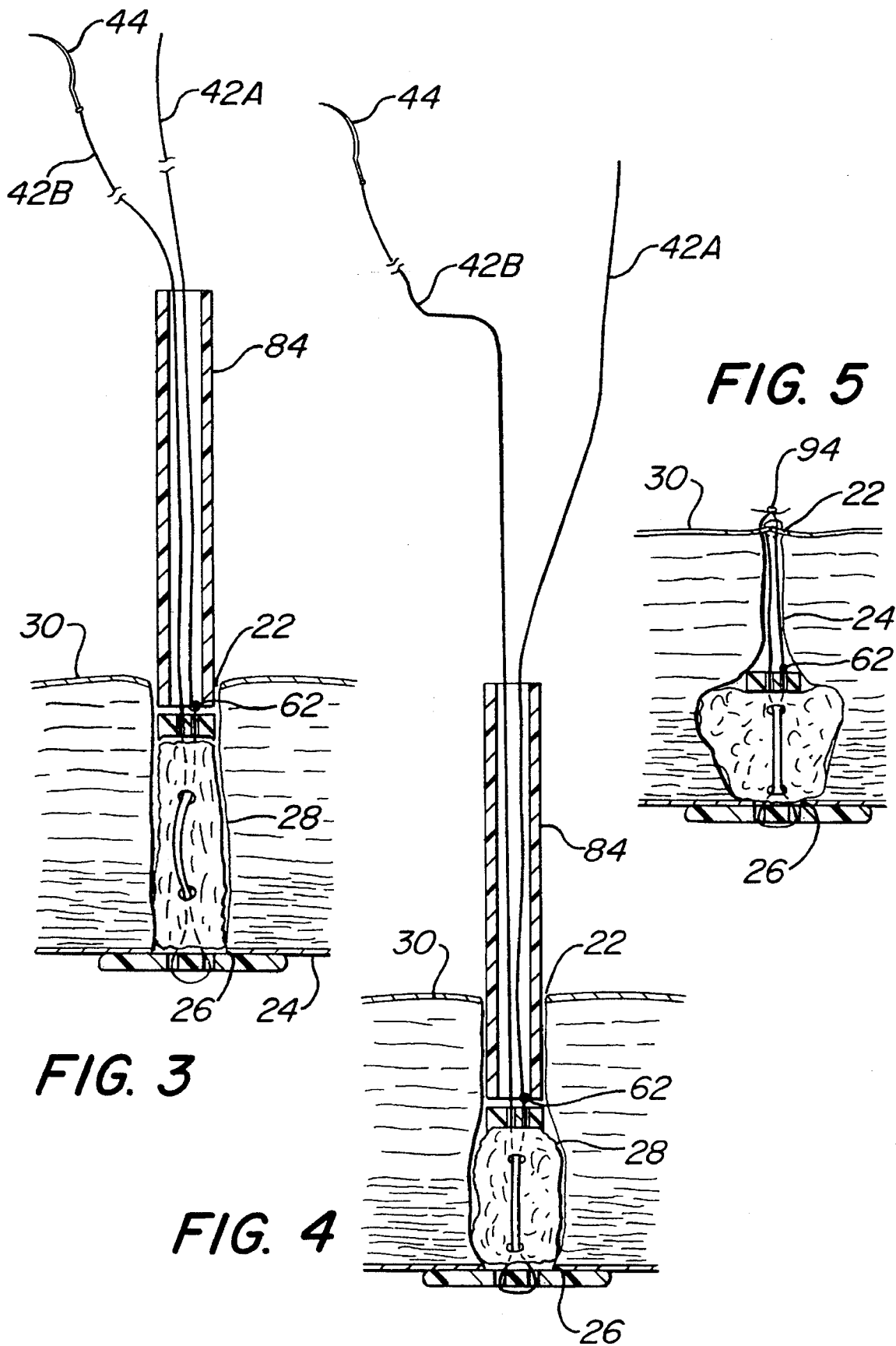

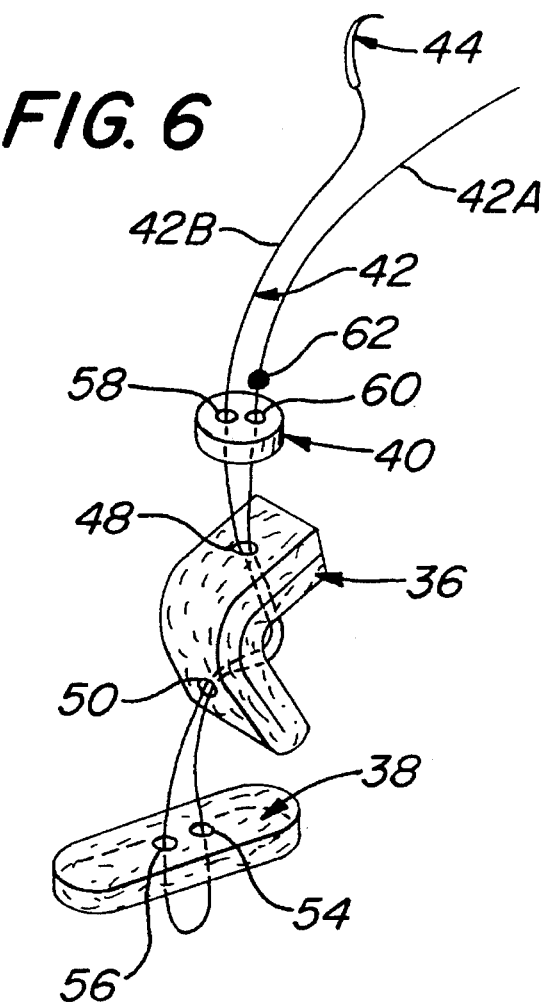
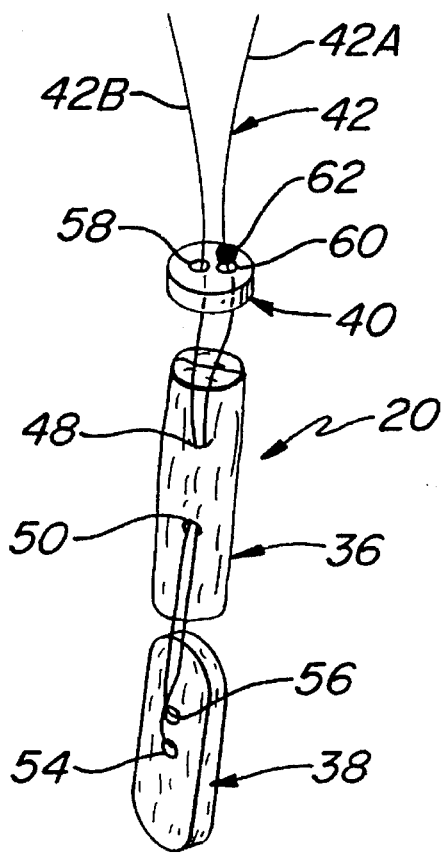
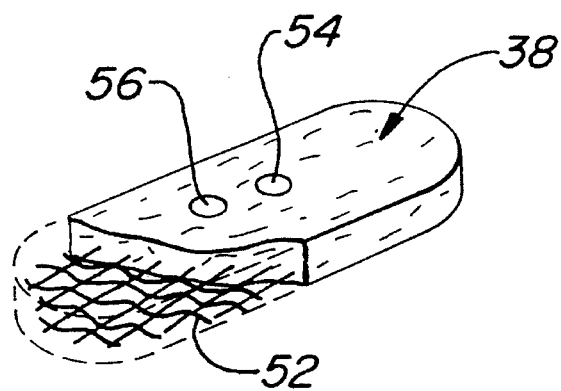
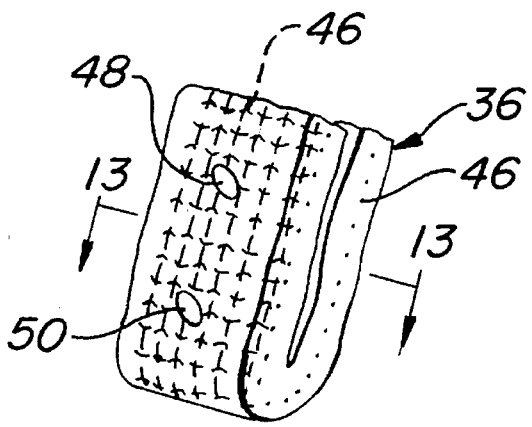

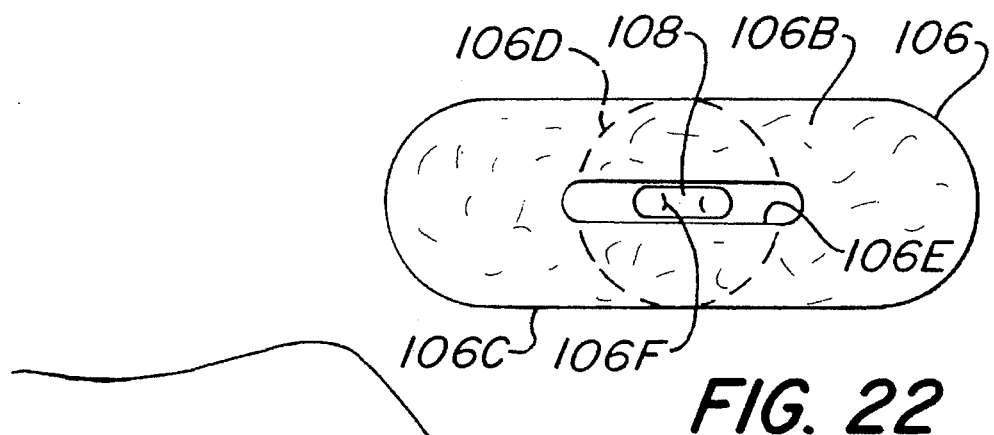
FIG. 22
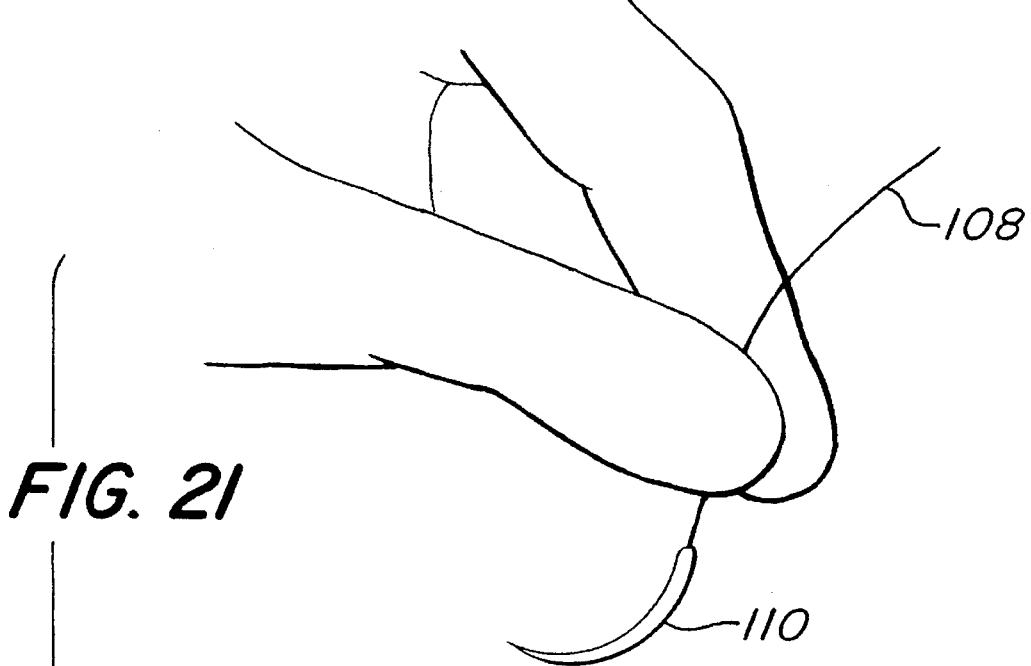
FIG. 21
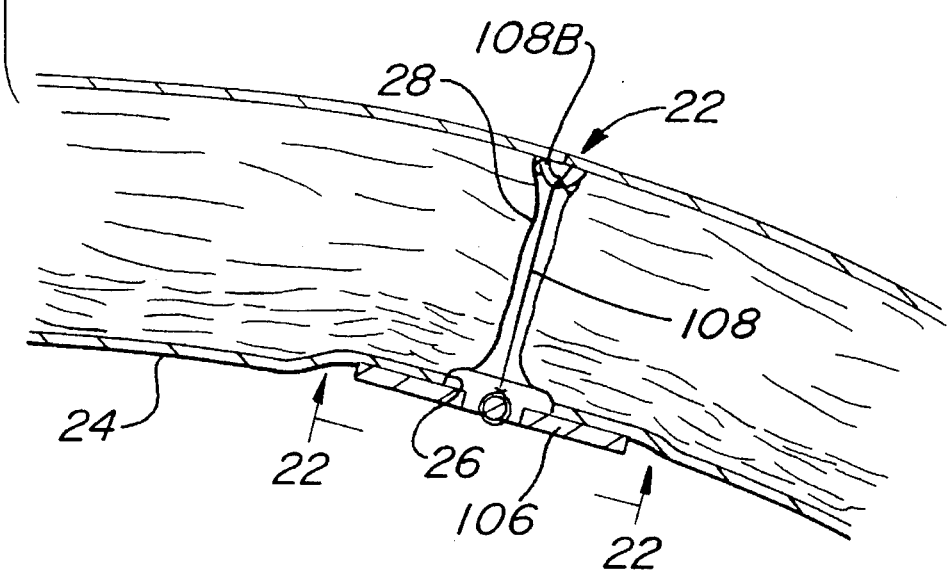

SYSTEM FOR CLOSING A PERCUTANEOUS PUNCTURE FORMED BY A TROCAR TO PREVENT TISSUE AT THE PUNCTURE FROM HERNIATING

This application is a continuation-in-part of U.S. application Ser. No. 08/235,825, filed on Apr. 29, 1994, pending, which is assigned to the same assignee as this invention, and whose disclosure is incorporated by reference. This application relates generally to laparoscopic surgical procedures, and more particularly to a system and method for sealing the percutaneous puncture formed by a trocar during such procedures in order to prevent tissue contiguous with the puncture from herniating thereafter.

BACKGROUND OF THE INVENTION

A hernia is one of the most common ailments of mankind. Basically, a hernia is a weakness or hole in the abdominal wall through which abdominal contents such as bowels may protrude. In general, it relates to the abnormal protrusion of an organ or part of an organ or a portion of tissue through an aperture in its containing cavity. The usual, but not the only, hernia that is typically treated is congenital in origin, called an indirect inguinal hernia, and is due to the failure of the inner lining of the abdomen, called the peritoneum, to seal itself at the opening of the inguinal canal. Inguinal or groin hernias normally occur at one or more of three locations. The first location is in the weakened wall of the inguinal floor of the abdomen in Hesselback's triangle. This type of hernia is called a direct hernia. The second type of hernia is an indirect hernia that occurs at the internal ring adjacent to the vas deferens as it exits the abdomen to become part of the spermatic cord. The third type is a femoral hernia that occurs adjacent and medial to the femoral blood vessels. All hernias represent a potentially life threatening condition and once diagnosed they should be repaired unless there is some contraindication.

There are several different traditional surgical techniques for closing a hernial defect. The surgical repair of an inguinal hernia is a common procedure which surgeons often perform on an outpatient basis. This procedure entails making a formal 3 to 6 inch incision directly adjacent to the hernial defect. The various layers of tissue are cut and pealed back as the hernia area is dissected. This cutting through so many layers of tissue may be extremely traumatic. Moreover, such large incisions require careful post operative care to prevent infection from the outside. Other disadvantages of the conventional hernia surgery are the extended recuperation time and a large unsightly scar. Many other complications are possible: those related to any incision, such as bleeding and infection, and those related to conventional hernia procedures, such as damages to bowel and bladder, nerves and large blood vessels.

A less invasive surgical procedure to repair hernias has been used in conjunction with a laparoscope. Typically a prosthetic patch is inserted down the length of a trocar and forced out of the tube and moved into a desired position. Post-operative problems are decreased by this procedure because of the smaller external wound left by the surgical tube. The patch, however, still can shift before tissue has grown onto it. The patch also can be sutured to the transversalis fiasco or peritoneum to minimize movement. It has typically been difficult to attach patches with sutures using the laparoscope because of difficulties in viewing and in maneuvering through the laparoscope. Thus, while the laparoscopic techniques for hernia repair have generally proven to be less invasive, they still leave something to be desired from the standpoint of effectiveness.

In addition to hernias that are congenital in origin, such as an indirect inguinal hernia, it has been found that external trauma as well as surgical intervention can lead to the formation of hernias. In this regard, it has been found that laparoscopic surgery, itself, can lead to a number of both local and general complications, such as herniation at the site of the percutaneous laparoscopic puncture with or without the formation adhesions thereat. In fact, it is estimated that herniation occurs in an appreciable percentage of these procedures within several months of the procedure. The herniation occurs because the muscle tissue at the location of the puncture is damaged during the procedure. This muscle tissue then weakens and due to internal pressure the intestines or other organs of the abdominal cavity are pushed through this weakened area. Such muscle failure results in a direct hernia, the repair of which typically requires a synthetic mesh to reinforce the damaged muscle tissue.

In U.S. Pat. No. 5,254,133 (Seid) there is disclosed a surgical implantation device arranged to be placed within a patient's body to seal an existing hernial rupture. The device is arranged to be used with a laparoscope to minimize the external wound necessary. The implantation device is arranged to be compressed into an implanting condition for placement at the opening in the transversalis fascia from the interior of the peritoneum using a laparoscope and then to be expanded into a deployed condition to securely seal the opening. The peritoneum can either be left intact and pushed through the fascia opening by the surgical tube and held in place by the surgical implant device at the peritoneum, or can be pierced and the surgical tube and device can be positioned directly in the fascia opening.

While the device of the Seid patent appears to overcome some of the short fallings of traditional surgical hernia repair by introducing the device into the abdominal cavity through a laparoscopic port and then positioned from the inside of the peritoneum outward to treat an existing inguinal hernia, it never the less has its own shortcomings. In this regard one shortcoming of the Seid device is that the laparoscopic procedure utilized to introduce the device for the repair of another hernia, is likely to become a site of a future herniation.

Other prior art relating to the use of reinforcing materials to be implanted at the site of weakened internal tissue to prevent herniation, are found in U.S. Letters Patent No. 5,092,884 (Devereux et al.); 5, 116,357 (Eberbach); 5,141, 515 (Eberbach); 5,220,928 (Oddsen et al.); 5,290,217 (Campos); and 5,274,074 (Tang et al.) but none of these are deemed to be suitable for effecting the prevention of post-laparoscopic herniation in a percutaneous puncture.

Thus, a need presently exists for a device and technique to assist in the prevention of post-laparoscopic puncture herniation and eliminate the need for future surgical intervention.

In U.S. Letters Patent No. 5,021,059, which has been assigned to the same assignee as this invention, and whose disclosure is incorporated by reference herein, there is disclosed a closure device and method of use for sealing a small incision or puncture in tissue separating one portion of the body of a living being from another portion thereof, e.g., a percutaneous puncture in an artery, to prevent the flow of a body fluid, e.g., blood, through the puncture. The closure device is arranged to be used with (deployed by) an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture. The closure device comprises three components, namely, an anchor member, a sealing member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam, and has a tissue engaging portion. The filament is connected between the anchor member and the sealing member in a pulley-like arrangement so that they may be moved relative to each other by the application of a pulling force on the filament. The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member causes the tissue engaging portion of the sealing member to move with respect to the anchor member, thereby drawing the anchor member and sealing member together. This action causes the tissue engagement portion of the sealing member to seal the puncture from the flow of fluid therethrough.

In copending U.S. patent application Ser. No. 07/846,322, filed on Mar. 5, 1992, entitled Hemostatic Puncture Closure System and Method of Use, also assigned to the same assignee as this invention, and whose disclosure is incorporated by reference herein, there is disclosed and claimed an improved system for sealing a percutaneous puncture in a blood vessel of a living being, with the puncture comprising an opening in the wall of the blood vessel and a tract contiguous with that opening and extending through tissue overlying the blood vessel. That system basically comprises carrier means, introducer means, and closure means. The closure means comprises anchoring means, sealing means, and filament means, with the filament means coupling the anchoring means and the sealing means. The introducer means comprises a tubular member having a distal free end insertable into the puncture tract and through the opening in the blood vessel wall. The carrier means is insertable through the introducer means and includes means to expel the anchoring means therefrom. Moreover, the carrier means is retractable with respect to the introducer means after the anchoring means has been expelled from the carrier means, so that when it is retracted it draws the anchoring means into engagement with the distal free end of the introducer means. The introducer means and the carrier means are coupled for movement together to draw the anchoring means which is now in engagement with the distal end of the introducer means into engagement with the interior tissue of the vessel generally adjacent the opening in the wall thereof. The filament means is operative to move the anchoring means and the sealing means relative to each other to cause the sealing means to engage tissue generally adjacent the puncture outside of the vessel.

In yet another copending application, Ser. No. 08/012,816, filed on Feb. 3, 1993, entitled Hemostatic Vessel Puncture Closure System Utilizing A Plug Located Within The Puncture Tract Spaced From The Vessel And Method Of Use, which is assigned to the same assignee as this invention, and whose disclosure is incorporated by reference herein, there is disclosed a further improved puncture closure system. That system basically comprises carrier means, introducer means, and closure means. The puncture comprises a tract extending through tissue overlying the blood vessel. In the preferred embodiment, the closure device comprises four components, namely, an anchor member, a sealing member, a spacer member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam. The spacer member is mounted upon the suture, and is slidable thereon, and is positioned between the anchor member and the sealing member. The filament member is connected between the anchor member and the sealing member in a pulley-like arrangement so that the members may be moved relative to each other by the application of a pulling force on the filament. The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member and the sealing member causes the sealing member to move with respect to said anchor member and into engagement with the spacer member thereby drawing the anchor member, spacer member and sealing member together. This action causes the sealing member to seal the puncture from the flow of fluid therethrough. The presence of the spacer member prohibits the sealing member from contacting the arterial wall and thereby possibly entering into the artery where a portion could conceivably break off and flow distally or cause the creation of an embolism.

In still another copending application, Ser. No. 08/064,192, filed on May 17, 1993, entitled Fail Predictable Reinforced Anchor For Hemostatic Closure, which is assigned to the same assignee as this invention, and whose disclosure is incorporated by reference herein, there is disclosed a further improved puncture closure system. In the preferred embodiment of the system specifically disclosed in that application the closure comprises an elongated rigid anchor member formed of a resorbable material, a sealing member formed of a resorbable material, e.g., compressed collagen plug, and a thin resorbable material filament, e.g., a suture, connecting the anchor member and the sealing member. The anchor member is located in the interior of the vessel, with the sealing member being located in the puncture tract. An elongated reinforcing filament or ribbon (either apertured or unapertured), formed of a resorbable material, is incorporated in the elongated anchor member to prevent any portion of it from breaking away in the event that the anchor is loaded beyond its breaking point.

It has been determined that the devices disclosed in the aforementioned applications, with some modifications, as well as other devices, some preferred embodiments of which are set forth hereinafter, can be used to effect the sealing of a percutaneous puncture formed during a laparoscopic procedure of the abdomen or an endoscopic procedure of the thoracic cavity, or some other minimally invasive procedure performed percutaneously. In the case of the sealing of a puncture in the peritoneum, the devices of this invention not only seal the puncture, but also block the egress of tissue therethrough. Thus, the likelihood of herniation is reduced. Moreover, the devices may include means to reinforce the tissue at the tissue opening so that the long-term strength of the scar tissue forming thereat is enhanced. This action may render the puncture site resistant to herniation in the long term.

OBJECTS OF THE INVENTION

Accordingly, it is a general object of this invention to provide devices and methods of use which address the needs of the prior art to seal an opening in internal tissue, e.g., the peritoneum, the thoracic cavity wall, or some other internal tissue, at the site of a percutaneous puncture.

It is another object of this invention to provide a device and method of use for extension through a percutaneous puncture into an opening internal tissue of a living being to seal that opening and reduce the risk of tissue gaining egress therethrough or of fluid flowing therethrough.

It is another object of this invention to provide a device and method of use for extension through a percutaneous puncture extending into the peritoneum to seal puncture, lessen the risk of a hernia forming thereat, and to increase the long-term strength of the scar tissue forming thereat.

SUMMARY OF THE INVENTION

These and other objects of this invention are achieved by providing a system and method of use for introducing a device through a percutaneous puncture into some internal tissue of a living being, e.g., the peritoneum, formed during a minimally invasive surgical procedure, e.g., a laparoscopic, endoscopic, or arthroscopic procedure, to seal the opening and/or prevent the egress of tissue into the puncture. The percutaneous puncture includes a puncture tract extending from the skin to the opening in the internally located tissue. The system includes a deployment instrument and a sealing device. The sealing device basically comprises anchoring means and filament means. The anchoring means is arranged to be extended through the tract and the opening and is orientable for engaging the interior of the internal tissue adjacent the opening to render the anchoring means resistant to passage back through the opening. The filament means is coupled to said anchoring means and includes at least a first portion located outside the internal tissue extending through the tract and coupled to the anchoring means and cooperating with the anchoring means for holding the anchoring means in place within the puncture. By so doing the anchoring means serves to block at least a portion of the opening.

In accordance with one method aspect of the invention the device is introduced into the puncture by the deployment instrument forming a portion of the system.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 3 is a side elevational view like FIG. 2 but showing the subject invention at subsequent time, i.e., immediately after the removal of the deployment instrument and trocar from the percutaneous puncture leaving the device of FIG. 1 in place;

FIG. 4 is a side elevational view like FIG. 3 but showing the subject invention at yet a further time, i.e., when a tamping component of the deployment instrument is used to deform a portion of the device of FIG. 1 in the percutaneous puncture;

FIG. 5 is a side elevational view like FIG. 4 but showing the device of FIG. 1 of the subject invention after it is fully installed within the percutaneous puncture;

FIG. 6 is an isometric view of the embodiment of the device of FIG. 1 of the subject invention during its fabrication;

FIG. 7 is an isometric view like that of FIG. 6 but showing the device of FIG. 1 in its completed state ready for disposition within the deployment instrument shown in FIG. 1;

FIG. 8 is an enlarged isometric view, partially broken away, of the anchor component of the device of FIG. 1;

FIG. 9 is an enlarged isometric view of the plug component of the device of FIG. 1;

FIG. 10 is an enlarged sectional view taken along line 10—10 of FIG. 1;

FIG. 11 is an enlarged sectional view taken along line 11—11 of FIG. 1;

FIG. 12 is an enlarged sectional view taken along line 12—12 of FIG. 1;

FIG. 21 is a sectional view taken along line 21—21 of FIG. 20;

FIG. 22 is a plan view of the sealing device of FIG. 14 shown fully in place as taken along line 22—22 of FIG. 20;

DETAILED DESCRIPTION OF THE PREFERRED EMBODIMENTS

Figure 1:
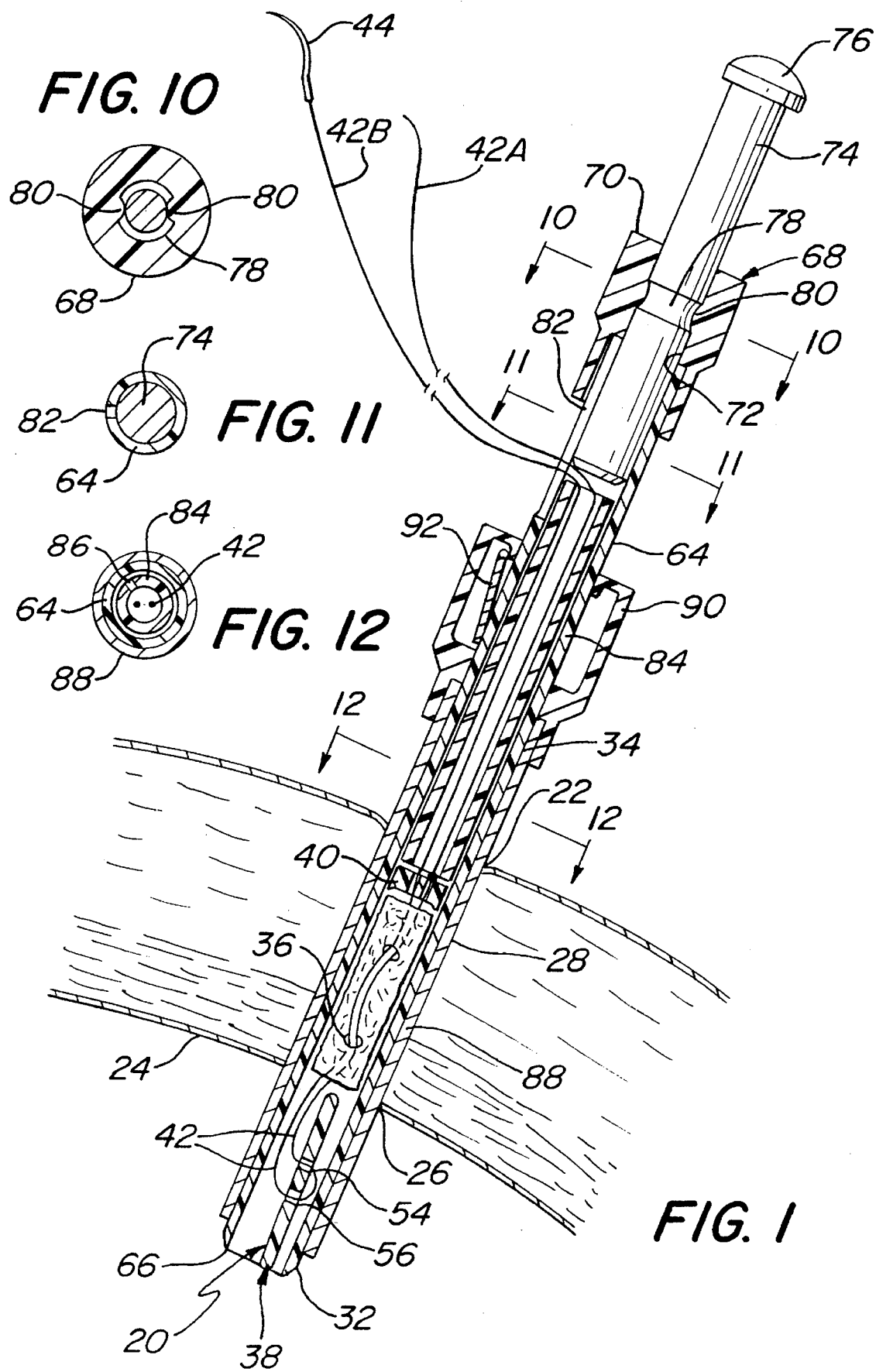
FIG. 1 is a side elevation view, partially in section, showing a trocar extending percutaneously into the abdomen of a living being, with a deployment instrument and one embodiment of a sealing device of the system of the subject invention located therein for placement of the device into the percutaneous puncture.

Referring now in greater detail to the various figures of the drawings wherein like reference characters refer to like parts, there is shown at 20 a device constructed in accordance with this invention for disposition within a percutaneous puncture 22 extending into penetratable internal tissue. In the embodiment shown herein the penetratable tissue comprises the peritoneum or the lining of the thoracic cavity, and that tissue is designated by the reference number 24. The percutaneous puncture includes an opening 26 in the tissue and a tract 28 extending from the surface of the skin 30 to the opening through the underlying tissue, e.g., the fat/fascia and muscle.

It should be pointed out at this juncture that while the device 20 and its deployment instrument 32 have particular utility when used in connection with minimally invasive surgical procedures, it is to be understood that the subject invention can be used to reinforce or otherwise enhance the long-term strength of scar tissue which may form at any internal puncture site and to prevent the passage of fluid or tissue through the puncture. Thus, while the description of the preferred embodiment instrument and device to follow is directed to the closing off of percutaneous incisions or punctures in the abdominal cavity or in the thoracic cavity, the subject invention has much more wide-spread applications.

As can be seen in FIG. 1 the device 20 is arranged to be extended into the puncture by means of a deployment instrument 32. The deployment instrument is arranged to be extended through a conventional or non-conventional trocar in order to place the device 20 in position. The trocar is shown schematically in FIG. 1 and designated by the reference number 34. It should be noted at this point that in some applications the use of a trocar may be obviated so that the deployment instrument 32, per se, can be inserted through the puncture to place the device 20 in the desired position within the puncture.

In any case the device 20 is arranged to be deployed into the puncture by the deployment instrument 32 so that a first portion of it (to be described later) is extended through the opening 26 and makes contact with the adjacent, e.g., contiguous, tissue, while a second portion of it (also to be described later) is within the puncture tract 28 to seal the puncture tract from the flow of fluid therethrough. As will also be described later one or both of those portions of the device include means, e.g., reinforcing means, so that the long-term strength of scar tissue which will form at the opening 26 is improved, thereby making that scar tissue resistant to subsequent herniation.

Referring now to FIGS. 1, 6, 7, 8, 9, and 13, it will be seen that the device 20 basically comprises four components, namely, a sealing member 36, an anchoring member 38, a holding member 40, and a positioning filament 42. A standard, conventional, e.g., curved stainless steel, needle 44 is secured to one end of the filament, and thus, may be considered as a fifth component of the device 20. The function of the needle 44 will be described later.

The sealing member 36 is deformable and is arranged to be located within the puncture tract and deformed therein to seal the tract from the flow of fluid therethrough. As best seen in FIGS. 6, 7, 9, and 13 the sealing member 36 basically comprises a strip of a compressible, resorbable, collagen foam, such as that sold by Colla-Tec, Inc. of Plainsboro, N.J. 08536. The strip of collagen foam includes a thin web or strip of a non-resorbable, e.g., dacron, reinforcing mesh 46 embedded within it. The mesh 46 serves to aid in reinforcing the scar tissue which forms adjacent the opening 26 in the tissue wall 24 when the plug member is in place. It should be pointed out at this juncture that other reinforcing materials, e.g., resorbable suture materials such as that sold under the trademark DEXON by Davis+ Geck of Wayne, N.J. 07470, can be used in the sealing member, if desired. The reinforcing materials can take various configurations, e.g., filaments, meshes, strips, bands, etc. In fact, if desired, it is contemplated that no reinforcing means be used in the sealing member 36, particularly if the anchoring member includes reinforcing means (to be described later). In the embodiment of the sealing member 36 shown herein the strip 36 is folded in two as shown in FIG. 9 and includes a pair of apertures 48 and 50 extending through the folded over strip. The apertures 48 and 50 are arranged to have portions of the filament 42 extended therethrough, as will be described later, to couple the various components of the device 20 to one another.

The folded over strip is arranged to be compressed from the state shown in FIG. 6 to that as shown in FIG. 7 so that the resultant plug member 36 is of reduced diameter, e.g., 8 mm, or width to fit within the deployment instrument as shown in FIG. 1.

The anchoring member 38 is arranged to be seated inside the penetrated internal structure, e.g., the peritoneum, against the tissue thereof adjacent, e.g., contiguous, with the opening 26 through which it had been introduced. As best seen in FIGS. 6–8 the anchoring member 38 is an elongated, low-profile component, similar to the anchor of the closure disclosed in the aforementioned copending patent applications, e.g., it may be formed of any resorbable material, such as a resorbable lactide/glycolide polymer sold by Medisorb Technologies International L.P. under the trade designation MEDISORB. The anchoring member is sufficiently rigid such that once it is in position within the abdominal cavity (as will be described later) it is resistant to deformation to preclude it from bending to pass back through the puncture through which it was first introduced.

In accordance with the preferred embodiment of the invention shown herein the anchoring member also includes reinforcing means, e.g., a strip or web 52 (FIG. 8) of a woven, non-resorbable mesh, such as dacron, embedded therein. The mesh serves to aid in reinforcing the scar tissue which forms adjacent the opening 26 in the tissue wall 24 when the anchoring member 38 is in place. It should be pointed out at this juncture that other reinforcing materials, e.g., resorbable suture materials such as that sold under the trademark DEXON by Davis+ Geck of Wayne, N.J. 07470, can be used in the anchoring member, if desired. The reinforcing materials can take various configurations, e.g., filaments, meshes, strips, bands, etc. In fact, if desired, it is contemplated that no reinforcing means be used in the anchoring member, particularly if the sealing member includes reinforcing means (described earlier). In the embodiment of the invention wherein the anchoring member is reinforced it serves to reinforce any scar tissue which will form in the immediately adjacent tissue.

The anchoring member 38 includes a pair of apertures 54 and 56 extending through it. These apertures are arranged to have portions of the filament 42 extended therethrough, as will be described later, to couple the various components of the device 20 to one another.

As can be seen in FIGS. 6 and 7 the holding member 40 is a disk-like member having a pair of apertures 58 and 60 extending therethrough. In accordance with a preferred embodiment of this invention the member 40 is rigid or stiff and is resorbable, e.g., is formed of the same material as that of the anchoring member. The apertures 58 and 60 are arranged to have portions of the filament 42 extended therethrough, as will be described later, to couple the various components of the device 20 to one another.

The filament 42 preferably comprises a very thin flexible member, e.g., a resorbable suture, which connects the anchoring member 38, the sealing member 36, and the holding member 40 in a pulley-like arrangement. In particular the filament is threaded through the aperture 58 in the holding member 40, from there through the aperture 48 in the plug member from one side to the opposite side thereof and out the aperture 50, from there into the aperture 56 in the anchoring member, from there out of aperture 54 in the anchoring member, from there in through the aperture 50 in the plug member from one side to the opposite side thereof and out the aperture 48, from there through the aperture 60 in the holding member 40. This arrangement produces a pair of proximal end portions 42A and 42B. A knot 62 is provided in the end portion 42A of the filament immediately proximally of the aperture 60 in the holding member 40. The needle 44 is connected to the free end of end portion 42B.

As can be seen clearly in FIG. 1 the end portions 42A and 42B of the filament 42 are arranged to extend out of the deployment instrument 32 when the device 20 is disposed therein. Accordingly, as will be described later when the device 20 is deposited in the puncture 22 by the deployment instrument the end portions 42A and 42B of the filament 42 extend out of the puncture tract 28. This arrangement enables the filament 42 to be manipulated to effect the proper seating of the device in place. Moreover, the ends 42A and 42B are arranged to be secured together, e.g., knotted by a conventional surgical knot, penetrating the tissue contiguous with the opening in the skin after the device is properly seated within the puncture to aid in holding or locking the device in place.

If desired, one or more additives, such as a radiopaque material or hemostatic agent or antibacterial agent, or any other biologically active ingredient, can be blended into or coated upon the holding member, the anchoring member, the filament member, or the sealing member or any combination thereof.

Referring now to FIG. 1 the details of the deployment instrument 32 will now be described. As can be seen therein the deployment instrument basically comprises an elongated tube or carrier 64 having an open distal free end 66 and a plunger assembly 68 located at the proximal end. The device 20 is disposed within the hollow interior of the carrier tube 64 adjacent its open free end 66, with the anchoring member 38 located immediately adjacent the free end and oriented so that its longitudinal axis is parallel to the longitudinal axis of the carrier tube. The sealing member is located immediately proximally of the anchoring member, and the holding member is located immediately proximally of the sealing member.

The plunger assembly comprises a cylindrical cap 70 having a central passageway 72 extending therethrough in axial alignment and communicating with the interior of the tube 64. An elongated, cylindrical plunger 74 is located within the passageway 72 in the cap 70. The proximal end of the plunger is in the form of an enlarged head or button 76. An annular recess 78 is provided about the periphery of the plunger. A pair of diametrically opposed nibs 80 (FIG. 10) project from the inner surface of the cap into the annular recess to hold the plunger in a retracted, "ready" position as shown in FIG. 1. A longitudinally oriented slot 82 (FIG. 11) is provided in the carrier tube 64 adjacent the cap 70 to enable the ends 42A and 42B of the filament to extend out of the deployment instrument.

A tamping member 84, in the form of an elongated sleeve, is disposed within the hollow interior of the carrier tube 64 between the holding member 40 and the distal end of the plunger 74. The sleeve includes a thin slot 86 (FIG. 12) extending along the length of the sleeve. The tamping member, being an elongated sleeve includes a central passageway extending fully therethrough. The end portions 42A and 42B of the filament are arranged to extend through the central passageway in the tamping member 84, as shown clearly in FIGS. 1 and 2.

Figure 2:
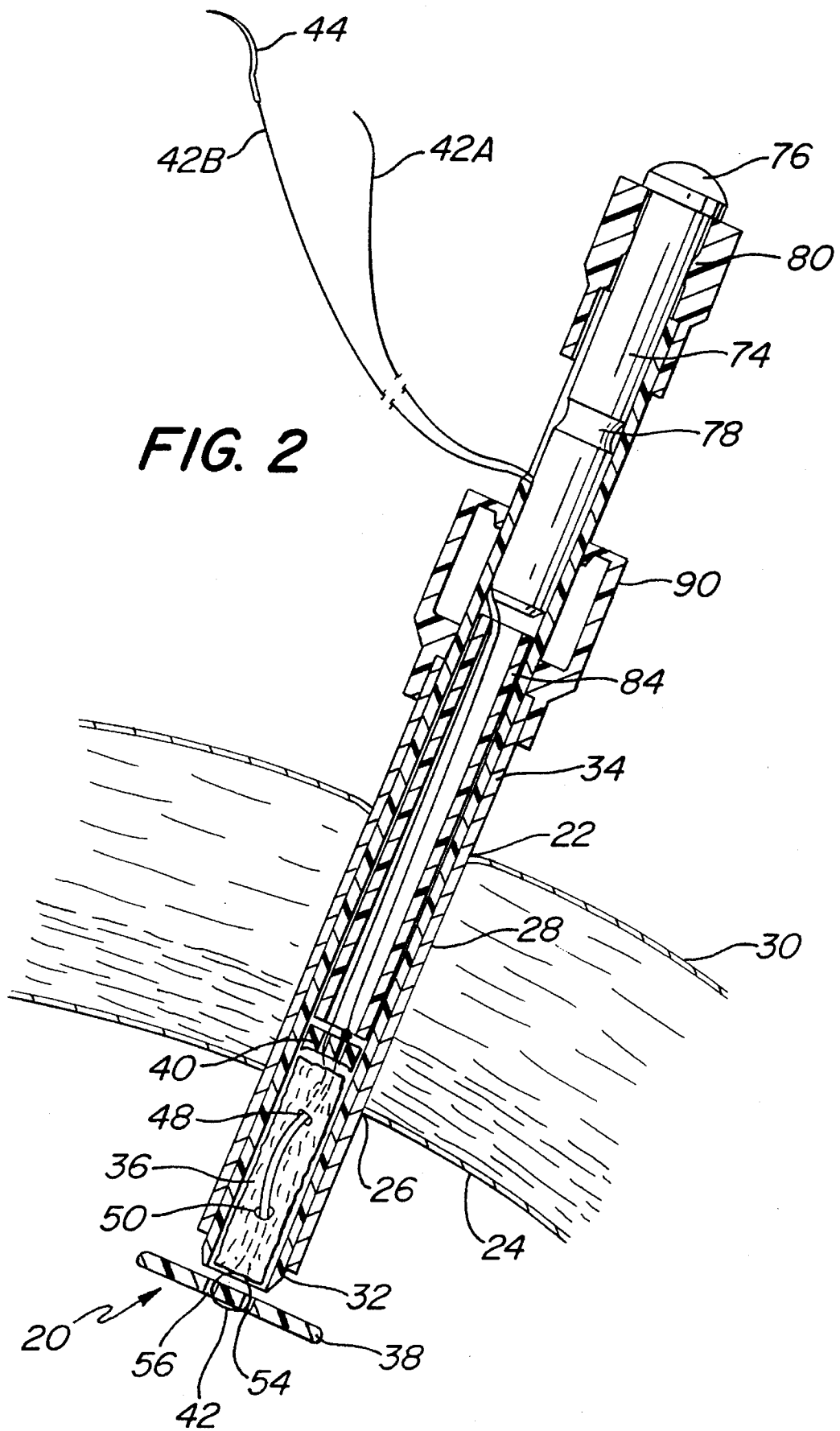
FIG. 2 is a side elevational view like FIG. 1 but showing the subject invention at an initial step in the ejection of a portion of the device of FIG. 1 from the deployment instrument.
Figure 13:
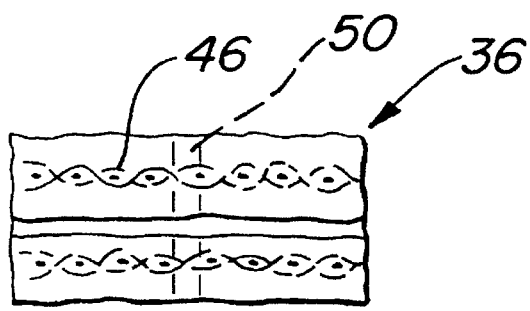
FIG. 13 is an enlarged sectional view taken along line 13—13 of FIG. 9.

As can be seen in FIG. 1 the trocar 34 basically comprises an elongated tube or sheath 88 formed of any suitable material, e.g., stainless steel. The sheath has an open distal end and a valve assembly 90 located at its proximal end. The valve assembly 90 includes any suitable valve member 92 to enable the deployment instrument to be inserted therethrough, as shown in FIGS. 1 and 2.

The device 20 of the subject invention is arranged to be used after the minimally invasive interventional procedure (e.g., laparoscopic, endoscopic, arthroscopic, procedure) is finished to seal the opening to prevent the passage of tissue or fluid therethrough and to enhance the long-term strength of the scar tissue which will naturally form at the opening 26 of the puncture 22 formed during the interventional procedure. To that end, the physician inserts the delivery or deployment instrument 32 containing the device 20 into the trocar 34 so that the distal end of the deployment instrument is extended through the opening 26 in the tissue wall as shown in FIG. 1. The plunger 74 of the deployment instrument is then depressed by pressing on its head or button 76 to release it from the ready position of FIG. 1 and move it distally, as shown in FIG. 2. This action causes the distal end of the plunger 74 to push on the proximal end of the tamping member 84, thereby moving the tamping member distally. This action, in turn, pushes on the holding member 40, the sealing member 36, and the anchoring member 38, to cause the anchoring member to pass out of the distal end of the instrument and trocar sheath, thereby deploying the anchoring member into the abdominal cavity.

The deployment instrument and trocar are then withdrawn from the puncture 22. This withdrawing action causes the anchoring member 38 to engage (e.g., catch) on the peritoneal wall contiguous with the opening 26. Continued withdrawal of the instrument and trocar deposit the sealing member 36, the holding member 40, and the distal end of the tamping member 84 of the deployment instrument into the puncture tract, as shown in FIG. 3. The tamping member is then grasped and gently pushed or tamped repeatedly into the puncture tract to push on the holding member. At the same time the free end of the filament 42 is pulled in the proximal direction. This combined action is shown in FIG. 4 and has the effect of moving the holding member 40 toward the anchoring member 38, thereby deforming the sealing member 36 therebetween. The knot 62 on the filament 42 adjacent the end portion 42A serves to hold the holding member 40 against the proximal end of the deformed sealing member.

As will be appreciated by those skilled in the art since the sealing member is formed of compressed collagen (or other hydrolytic material) it expands automatically in the presence of blood or body fluids within the puncture tract when deployed, thereby further contributing to its deformation, e.g., enlargement, within the puncture tract. In addition the expansion/deformation of the sealing member serves to aid in securing the device 20 in place. Thus, it is contemplated that in some applications the deformation/expansion of the sealing means will serve as the only or primary means for securing the device in place within the puncture.

Moreover, for some applications it is contemplated that the holding means 40 may be constructed like the compressible disk locking mechanism of the intravascular puncture closure disclosed in copending U.S. patent application, Ser. No. 08/072,293, filed on Jun. 4, 1993, entitled A Hemostatic Vessel Puncture Closure With Filament Lock, which is assigned to the same assignee as this invention and whose disclosure is incorporated by reference herein. The puncture closure of that application includes an anchoring member, a sealing member or plug of collagen foam, the locking mechanism, and a filament. The filament connects the anchoring member located within the interior of an artery with the plug in the puncture tract in a pulley-like arrangement so that the plug is movable toward the anchoring member. The compressible disk locking mechanism is arranged to be actuated, e.g., compressed, within the puncture tract to engage the filament in such a manner that the plug is held in the puncture sealing position. It is also contemplated that the filament and the anchoring means of this invention can be constructed like those locking mechanism components of the aforementioned copending application, wherein the anchoring means includes a notched passageway through which the filament extends and the filament comprises a portion having plural projections or teeth thereon adapted to slide into the notched passageway of the anchoring means in one direction but resistant to sliding in the opposite direction.

In any case, when the sealing member is in place within the puncture tract as described above it has the effect of sealing the puncture tract from the flow of fluid therethrough, while also preventing tissue from gaining egress therethrough. For example, in the case of thoracic placement the sealing member will prevent ingress of air into or out of the thoracic cavity. In the case of peritoneal placement the sealing member will prevent the egress of blood or some other body fluid out of the abdominal wall, while also preventing any tissue from gaining egress through the opening in the peritoneum.

Once the sealing member has been deformed and placed as just described, the tamping member 84 is then removed from the puncture tract 28. To that end the extending portions 42A and 42B of the filament 42 are slid through the tamping member's longitudinally extending slot 86, thereby freeing the tamping member from the device 20. The end portions 42A and 42B of the filament extending out of the puncture tract are then knotted together. In particular, using standard surgical techniques, the filament end 42B with the stainless steel needle 44 is used to suture the skin 30 surface contiguous with the puncture 22 to form a conventional surgical knot 94 and thereby secure the device in place.

Figure 14:
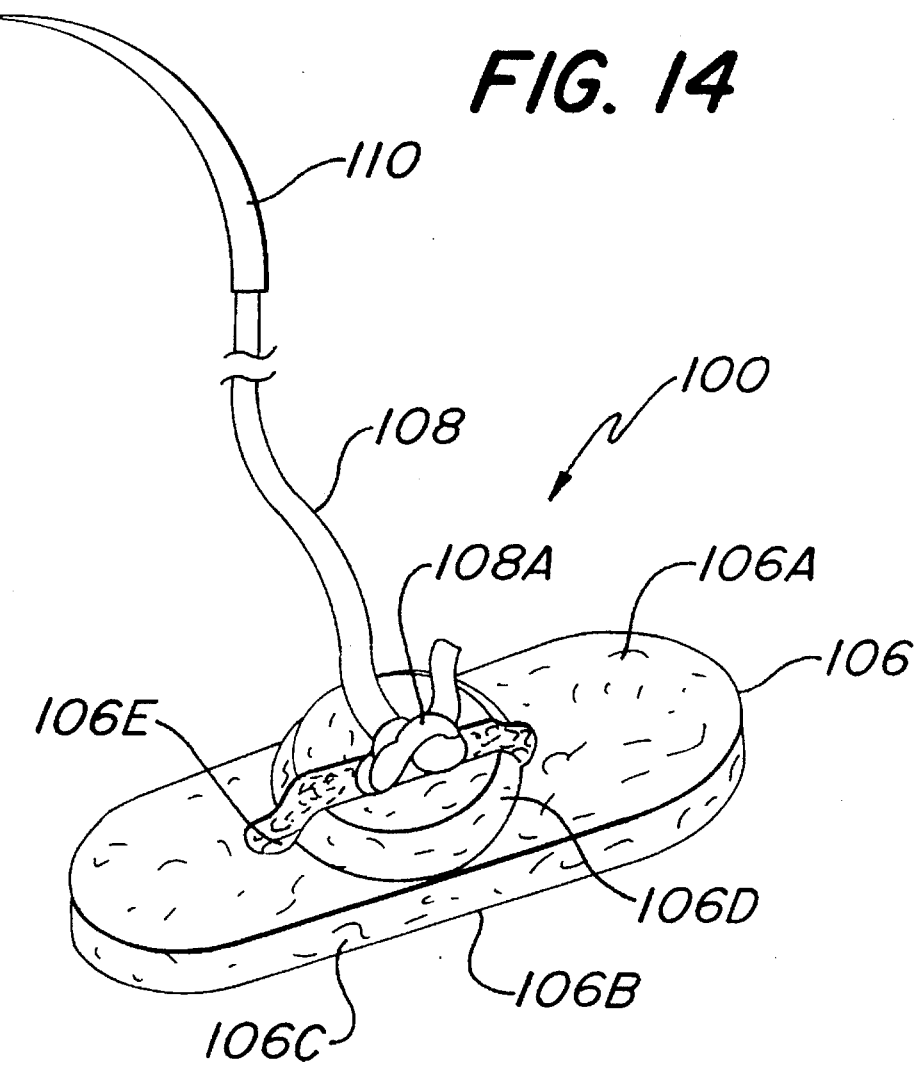
FIG. 14 is an enlarged isometric view of an alternative embodiment of a sealing device constructed in accordance with the subject invention.

In FIG. 14 there is shown an alternative embodiment 100 of a device constructed in accordance with the subject invention. The device 100 can be used in any of the applications as discussed with reference to the device 20, and can be deployed through any type of trocar, by any type of deployment instrument. In FIGS. 15–20 the device 100 is shown being deployed through a trocar 102, by a deployment instrument 104. For some applications it may not be necessary to utilize any trocar to effect the placement of the device 100 within the percutaneous puncture.

Figure 15:
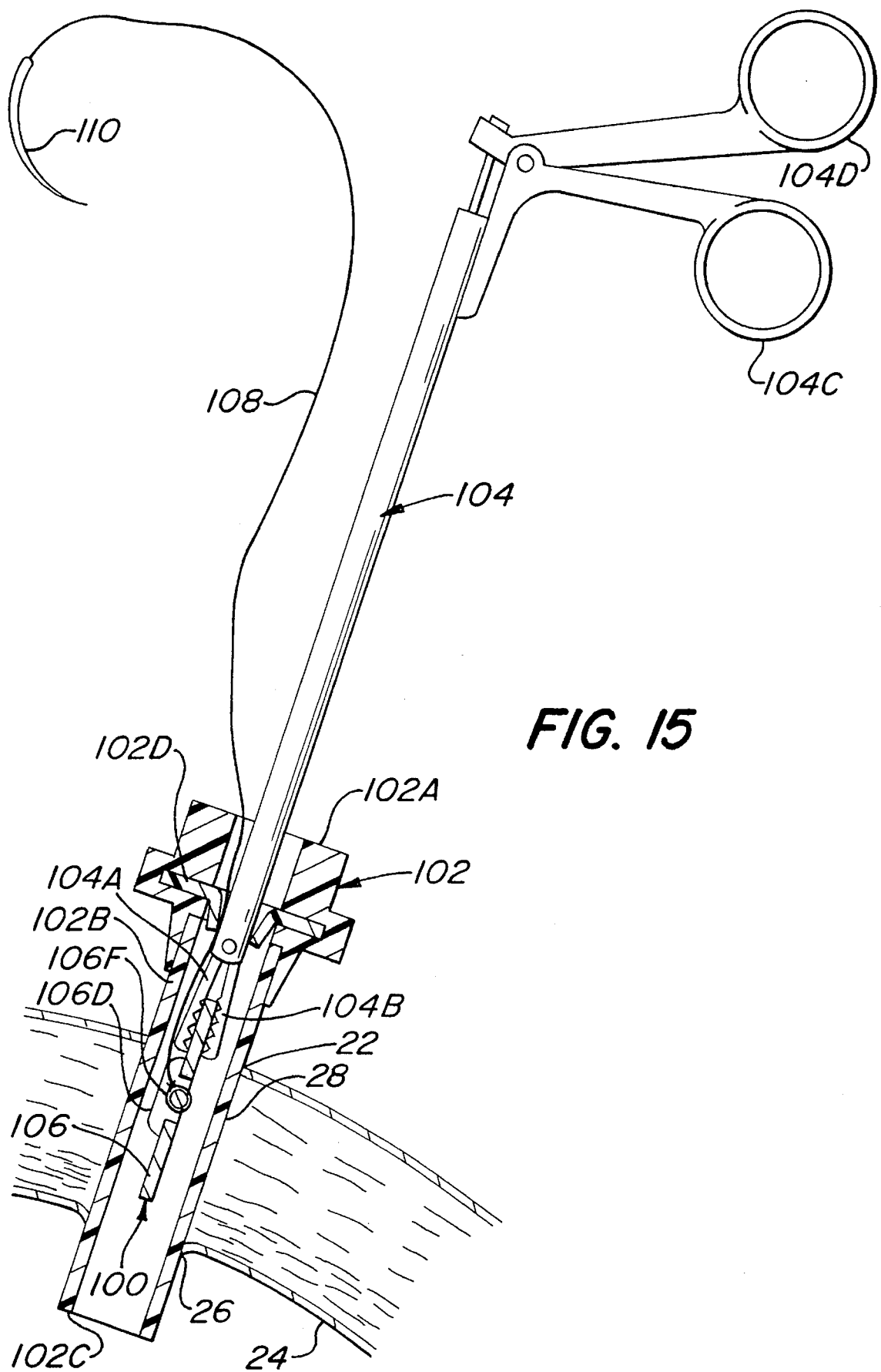
FIG. 15 is a side elevation view, partially in section, showing a trocar extending percutaneously into the abdomen of a living being, with a conventional grasper used as a deployment instrument extending through the trocar deploying the embodiment of the device of FIG. 14 into a percutaneous puncture.

Before describing the device 100 and its method of use, a brief description of the trocar 102 and the deployment instrument 104 is in order. To that end, as can be seen in FIG. 15 the trocar 102 is a conventional device, e.g., one sold by Apple Medical Corp. of Bolton, Mass., and basically comprises a hollow cap 102A from which a elongated tube or sheath 102B formed of any suitable material projects. The sheath is arranged to pass through the percutaneous puncture and terminates in an open distal end 102C communicating with the interior of the patient's body, e.g., the interior of the abdomen, when the trocar is in place. The trocar includes a hemostatic valve 102D located at within the hollow cap 102A. The valve is arranged to enable the deployment instrument 104 to be inserted therethrough, as shown in FIG. 15. Other conventional, or non-conventional type trocars can be used to enable the device 100 to be deployed into a puncture tract in accordance with this invention.

The deployment instrument 104 is also a conventional device, e.g., a conventional "grasper" sold by various companies, and basically comprises a pair of pivotable jaws 104A and 104B at the distal end of the instrument and a pair of squeezable handles 104C and 104D mounted at the proximal end of the instrument. By squeezing the handles together the jaws close, whereas release of the handles causes the jaws to open. Other instruments can be used as deployment devices, as well, providing they include means for holding the anchoring member to enable it to be inserted through the percutaneous puncture and then released from the instrument so that the anchoring member can be retracted against the desired tissue, as will be described later.

Referring now to FIG. 14 it will be seen that the device 100 basically comprises three components, namely, an anchoring member 106, a positioning filament 108, and a suturing member or needle 110. The anchoring member 106 is somewhat similar in construction to the anchoring members disclosed in the aforementioned U.S. patent applications and U.S. Pat. No. 5,021,059 assigned to the same assignee as the subject invention, and like the anchoring member 38 described heretofore is arranged to be seated inside the penetrated internal structure, e.g., the peritoneum, against the tissue thereof adjacent, e.g., contiguous with the opening 26 through which it had been introduced, as will be described later. Thus, as can be seen the anchoring member 106 is an elongated, low-profile component which is, preferably, sufficiently rigid such that once it is in position within the abdomen (as will be described later) it is resistant to deformation to preclude it from bending to pass back through the opening in the peritoneum and through the contiguous puncture tract. The member 106 has a generally planar top surface 106A, a radially contoured bottom surface 106B and a peripheral side surface 106C. Each end of the member 106 is rounded and the side surface of the member tapers inward slightly from its top surface to its bottom surface to facilitate its removal of it from the mold making it. A dome-like projection 106D is located at the center of the top surface of the anchoring member, with the top of the dome being flatted. A longitudinally extending slot 106E extends through the dome 106D of the anchoring member 106 and the underlying portion of the anchoring member to the bottom surface of the anchoring member as shown in FIGS. 14–20. A rod-like hub 106F (FIGS. 15–20) extends transversely across the slot 106 and serves as the means for securing the filament to the anchoring member, as will be described later.

In accordance with a preferred embodiment of the anchoring member 106, it may be constructed of the same material as that of anchoring member 38. Alternatively, it can be constructed of a 100% polyglocolide in place of the 50—50 polylactidecoglycolide resorbable polymer disclosed earlier. Moreover, the anchoring member 106, like anchoring member 38, need not be resorbable at all. Thus, it is contemplated that the anchoring members of this invention be constructed of a non-resorbable material, such a TEFLON®.

It should be noted that the anchoring member 106 shown herein does not include any reinforcing means, like that of anchoring member 38. However, it may, if desired, include such means, depending upon the application it is to be put. For example, if it is desired to reinforce the opening in the peritoneum to strengthen the scar tissue forming thereat, and thus lessen the likelihood that a hernia will form at that site at some time in the future, the sealing device may include the heretofore identified and described reinforcing means.

Moreover, like the device 20, one or more additives, such as a radiopaque material, or hemostatic agent, or antibacterial agent, or an anti-adhesion agent, or any other biologically active ingredient, can be blended into or coated upon the anchoring member 102 or the filament member or any combination thereof.

The filament 108 preferably comprises a very thin flexible member, e.g., a resorbable suture, which connects the anchoring member 106 to the suturing needle 110. To that end, as clearly can be seen in FIG. 14, the distal end of the filament 108 is extended into the longitudinally extending slot 106E, wrapped about the hub 106F, and formed into a knot 108A. The proximal end of the filament is secured to the needle 110. The needle is arranged to be removed from the filament after the device 100 has been deployed and secured, as will be described later. Thus, the needle may be releasably secured to the filament, or the filament may be severable so that it can be cut or otherwise severed to remove the needle therefrom. The needle 110 may be of any shape and construction, e.g., a standard, conventional, curved stainless steel needle.

The sealing device 100, like the device 20 described heretofore, is arranged to be used after the minimally invasive interventional procedure (e.g., laparoscopic, endoscopic, arthroscopic, procedure) is finished. For example, when used after a laparoscopic procedure it blocks the opening 26 in the peritoneum to reduce the risk of herniation in the short term. It may also reduce the long term risk of herniation, particularly if it includes reinforcing means, by enhancing the long-term strength of the scar tissue which will naturally form at the opening. When used for thoracic applications, the placement of the device 100 in the percutaneous puncture, precludes air from gaining ingress into the thoracic cavity through the puncture tract.

Figure 16:
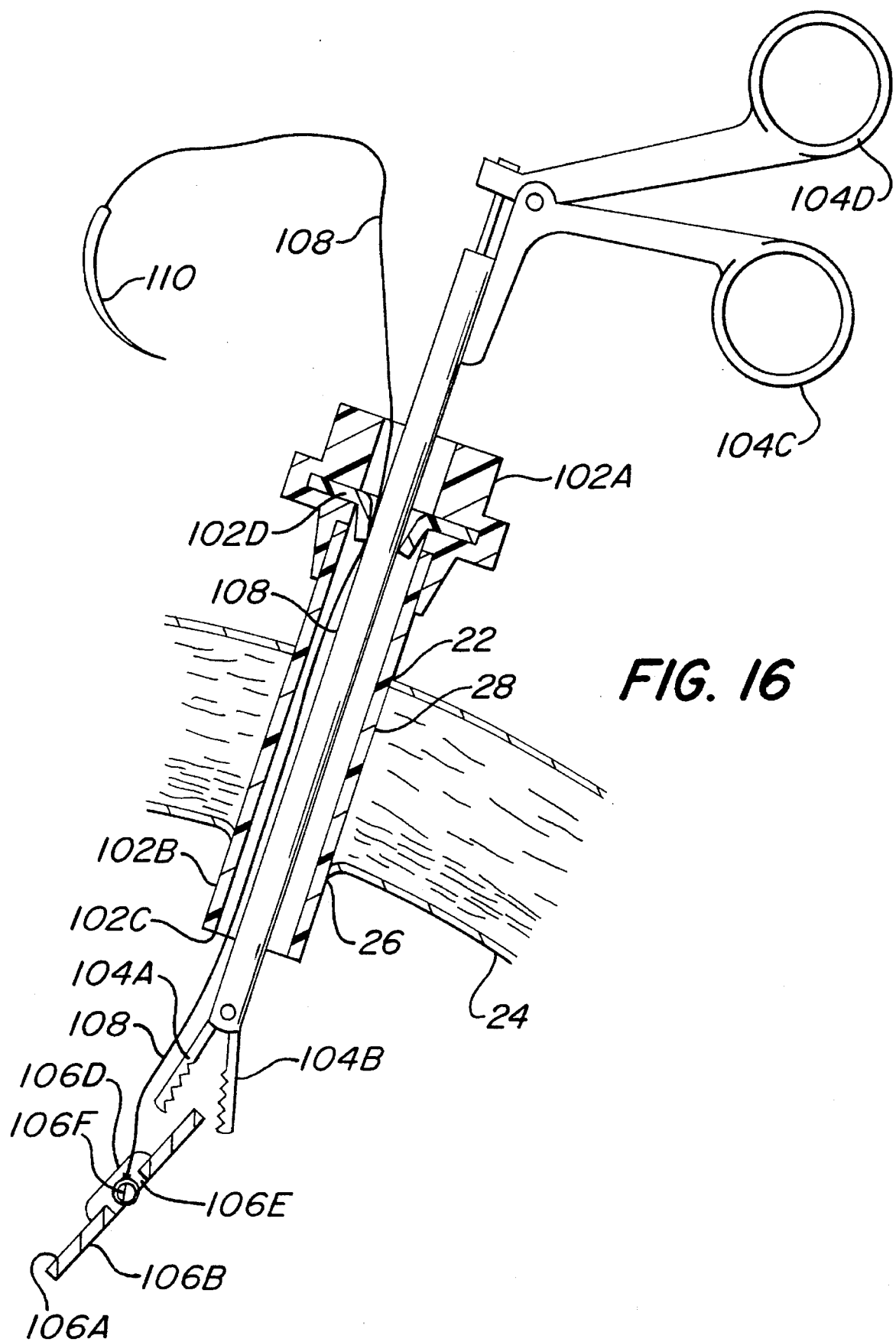
FIG. 16 is a side elevational view, like FIG. 15, but showing the device of FIG. 14 being released from the deployment instrument.
Figure 17:
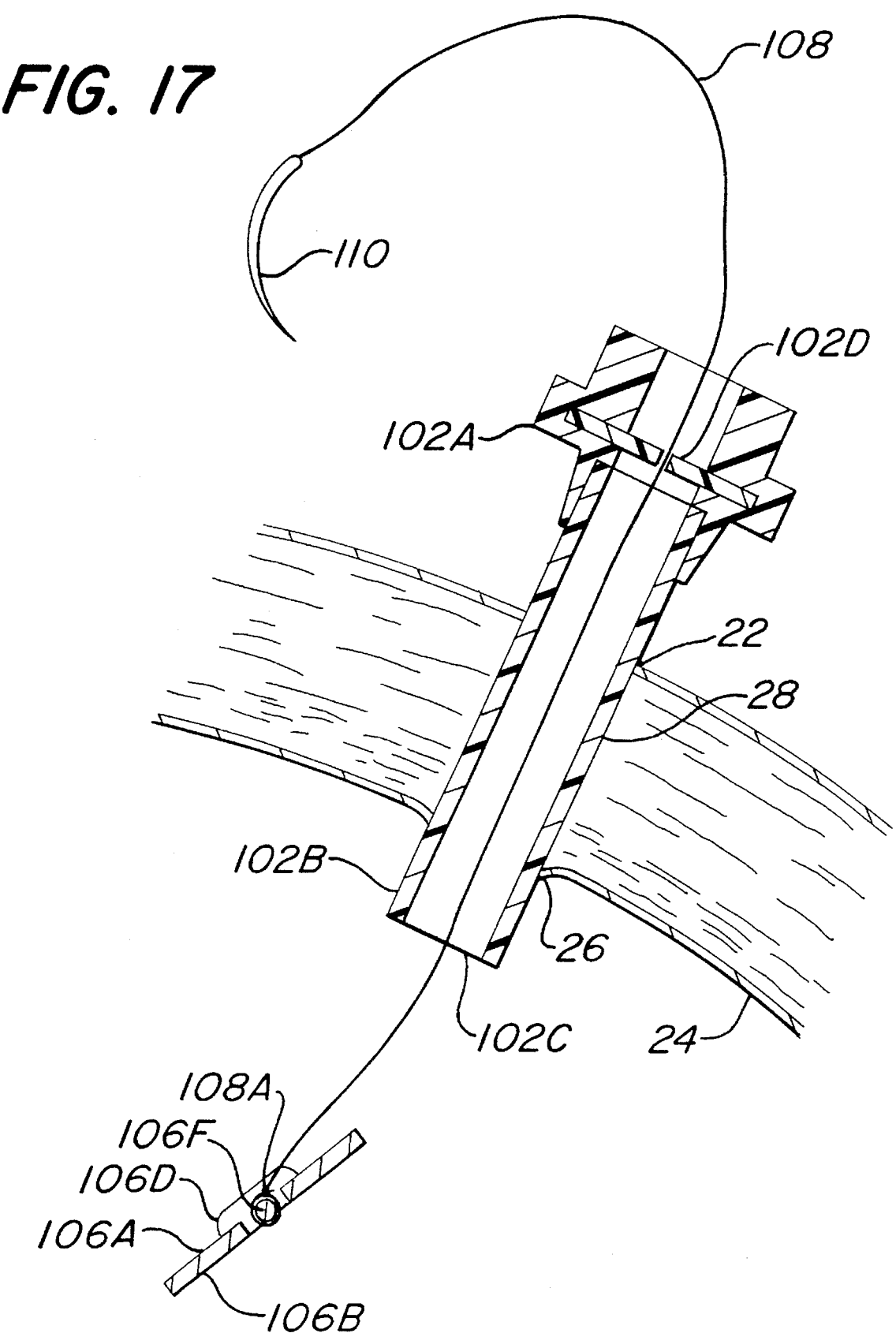
FIG. 17 is a side elevational, view like FIG. 16, but showing the device of FIG. 14 at subsequent time, i.e., immediately after the removal of the deployment instrument from the percutaneous puncture leaving the device in within the abdomen.

The use of the device 100 is as follows: with the trocar in place extending through the puncture so that its distal end 102C is within the abdomen, the physician utilizes the grasper 104 to grasp one end of the anchoring member 106 of the device 100 between its jaws 104A and 104B. The anchoring member is then inserted into the proximal end cap 102A of the trocar 102 through its valve 102D so that the anchor is within the interior of the sheath as shown in FIG. 15. The proximal portion of the filament 108 with the needle 110 thereon remains outside of the trocar, with the intermediate portion of the filament extending through the valve 102D. The grasper is then moved in the distal direction until the anchoring member and the jaws are fully within the abdomen, as shown in FIG. 16, whereupon the grasper's handles 104C and 104D are released. This action opens the jaws and releases the anchoring member from the grasper, as shown. The anchoring member, being coupled to the trocar, is thus not free within the abdomen since the filament extends through the valve 102D and is trapped thereby.

Figure 18:
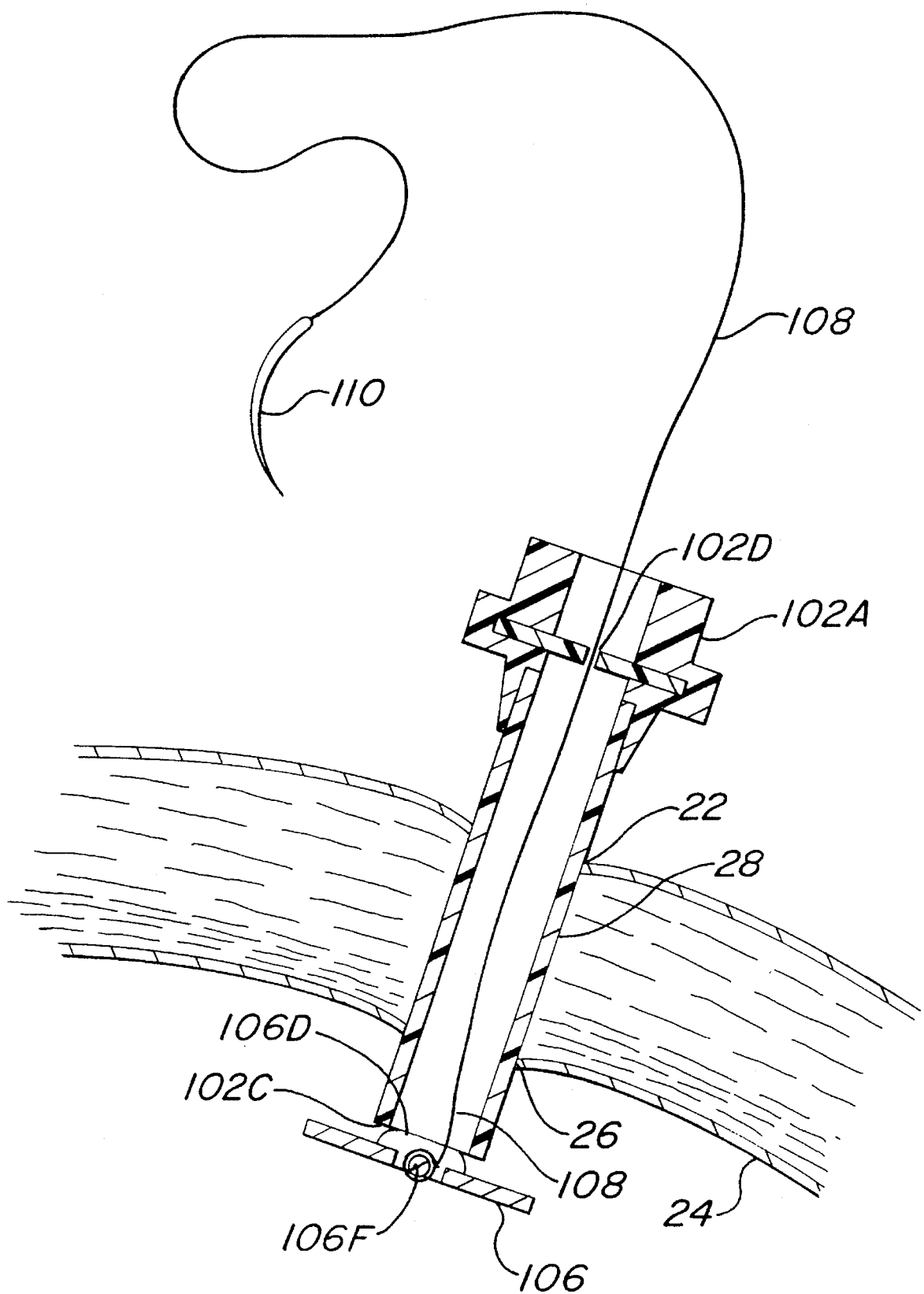
FIG. 18 is a side elevational view, like FIG. 17, but showing the device of FIG. 14 at yet a further time when a portion of the device is retracted against the distal end of the trocar.

The handles of the grasper are then squeezed together, whereupon the jaws close. The grasper is then retracted out of the trocar, leaving the device 100 in the position shown in FIG. 17, i.e., with the anchoring portion within the abdomen, and the middle of the filament trapped between the now-closed valve 102D of the trocar. The proximal end of the filament 108 is then pulled in the proximal direction to draw the anchoring member 106 against the free end 102C of the trocar, to trap it thereon as shown in FIG. 18. As can be seen therein when the anchoring member is "trapped" on the distal end of the trocar the longitudinal axis of the anchoring member is oriented generally parallel to the peritoneum contiguous with the opening 26. Then the trocar and the anchoring member are moved or retracted proximally as a unit until the top surface of the anchoring member engages the inner surface of the peritoneum contiguous with the opening therein. At this time the domed portion 106D of the anchoring member enters into the opening 26. This action effectively traps the anchoring member across the opening 26. Once the trocar has been removed from the puncture the puncture closes somewhat.

Figure 19:
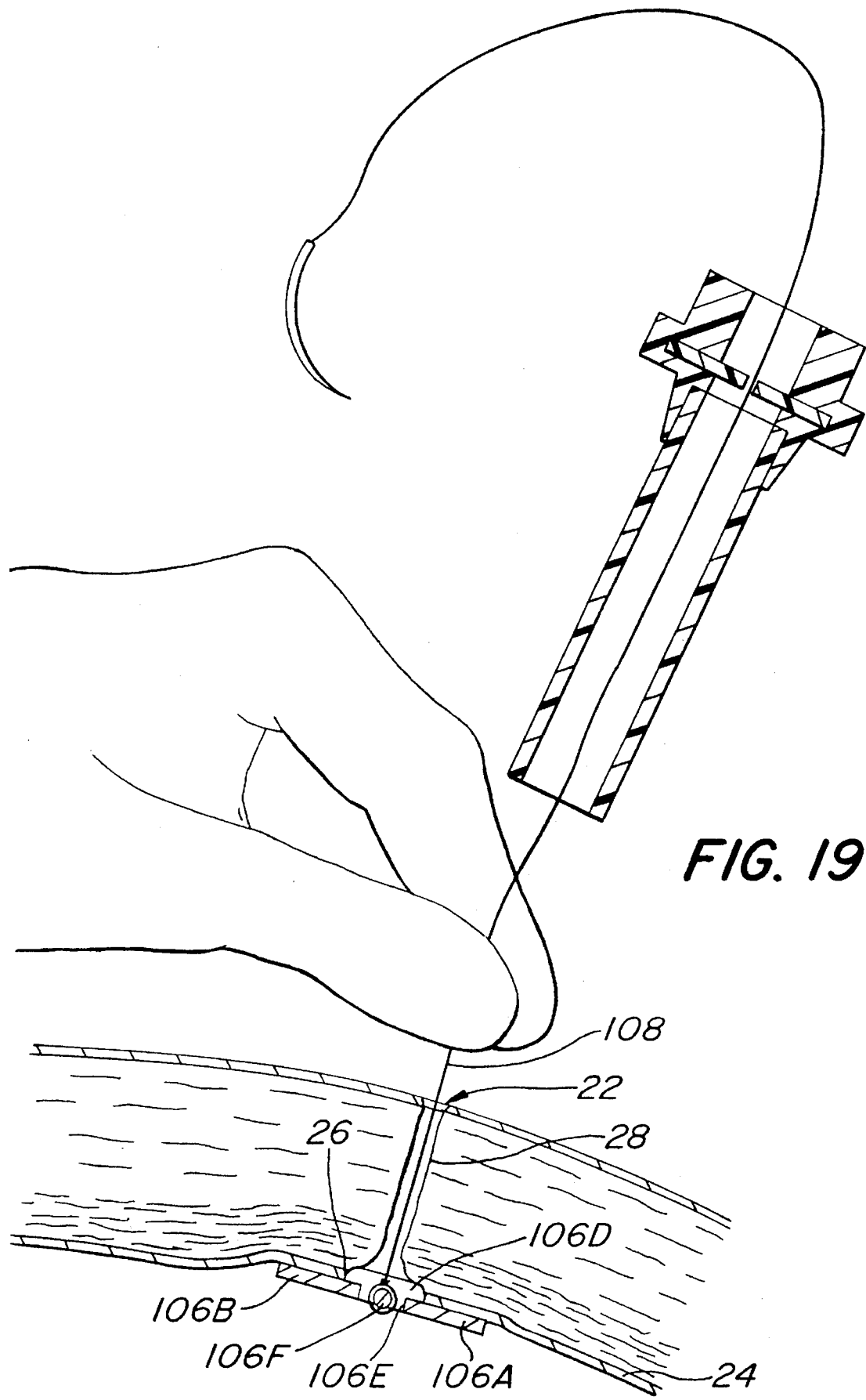
FIG. 19 is a side elevational view, like FIG. 18, but showing the device of FIG. 14 brought up against the inner surface of the peritoneum over the opening in the percutaneous puncture.

The trocar is then removed, i.e., slid off of the proximal end of the filament and needle, while tension is maintained on the filament to keep the anchoring member in position extending across the opening 26 in the peritoneum, with the domed portion within the opening, as shown in FIG. 19. Depending upon the size of the anchoring member and the degree which the opening 26 in the peritoneum shrinks or closes when the trocar is removed therefrom, the anchoring member 106 may completely cover the opening, thereby sealing the opening, or only partially cover it.

In a preferred embodiment of this invention the anchoring member is approximately 10 mm wide so that it will just fit within a 10 mm trocar. Thus, with a 10 mm wide anchoring member and a 10 mm, thin walled trocar, when the trocar is removed from the puncture the periphery of the opening 26 in the peritoneum will close in to engage the periphery of the domed portion 106D of the anchoring member, and with the anchoring member totally covering the opening 26, thereby sealing the puncture as shown by the phantom lines in FIG. 21.

Figure 20:
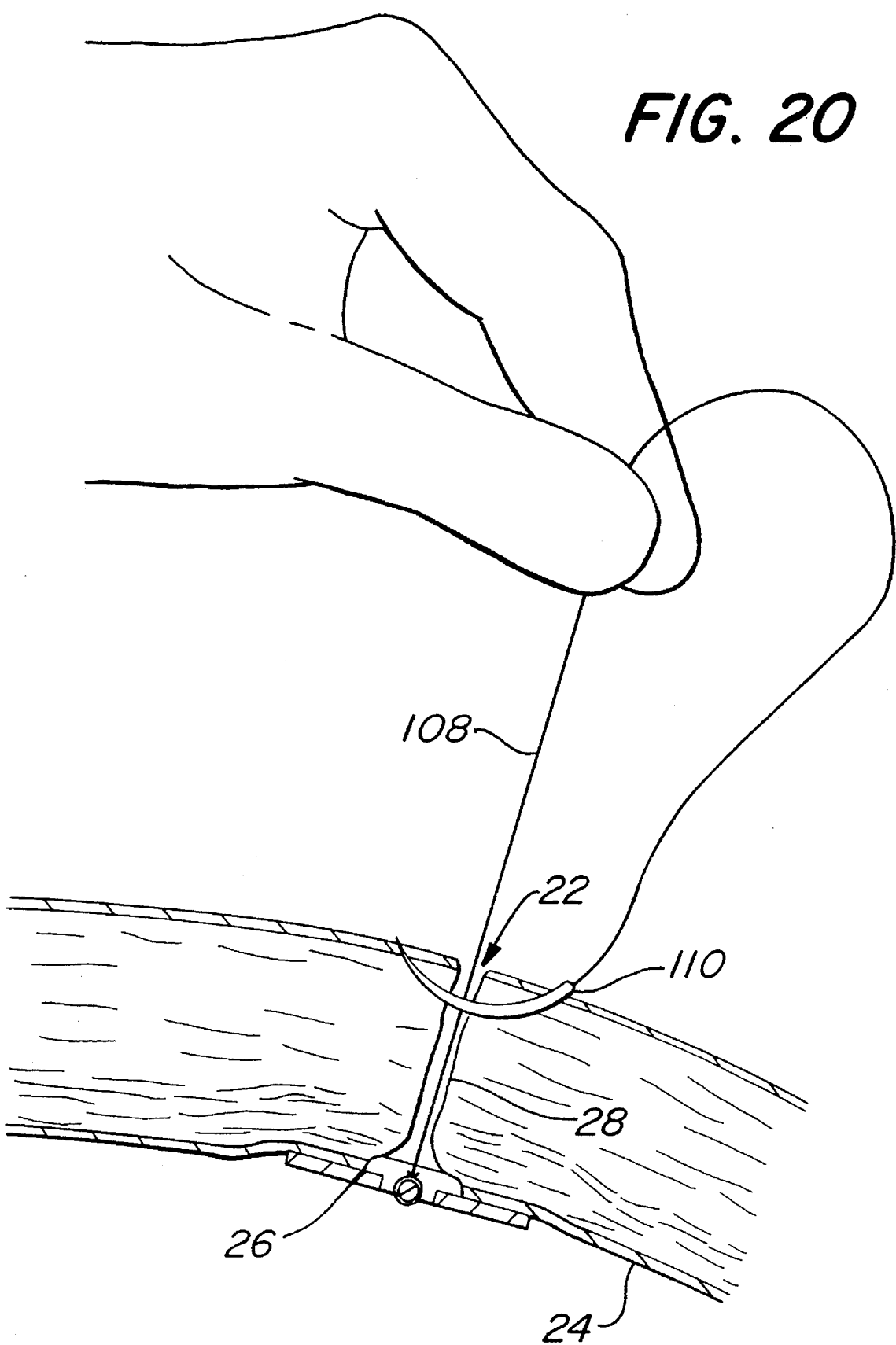
FIG. 20 is a side elevational view, like FIG. 19, but showing the device of FIG. 14 being sutured in place to fully install it within the percutaneous puncture.

Irrespective of the width of the anchoring member once it is trapped up against the inner surface of the peritoneum over the opening the needle 110 is then utilized to sew or suture the filament to the skin and underlying fascia contiguous with the puncture tract, thereby fixedly securing the device 100 in place, as shown in FIG. 20. Alternatively, the filament 108 may be sutured to any suitable tissue within the puncture tract below the skin using the attached needle 110. The puncture tract may be sutured closed at the skin by a separate conventional suture. Alternatively, the filament 108 may be arranged so that it includes two extending portions 108B and 108C, like shown in FIG. 23, with one of the extending portions 108B having the needle 110 secured thereto and with the other extending portion being free. Alternatively, the free ends of both extending portions 108B and 108C may include respective needles 110 thereon. In any case, the two extending portions can be secured to the skin or the underlying tissue in the puncture tract by suturing the extending portion 108B through that tissue using the attached needle and then knotting the two extending portions together using any conventional surgical technique.

It should be pointed out at this juncture that in accordance with another embodiment of the sealing device 100 the filament 108 may be knotted to the hub 106A of the anchoring member 106 in such a manner so that a pair of end portions of the filament extend from the anchoring member 106 instead of only one as shown in FIG. 14. In such an alternative embodiment, one of the two end portions has the needle 110 secured to its free end. This alternative embodiment enables both of the filament ends to extend out of the puncture tract when the device is in place so that the surgeon may grasp both of the ends to knot them together when suturing the filament to the skin and/or underlying tissue to secure the sealing device 100 in place.

Once the filament 108 (or the pair of filament ends) is sutured to the skin and/or tissue contiguous with the puncture tract, the needle 110 is removed from the filament 108, completing the puncture sealing procedure.

Figure 23:
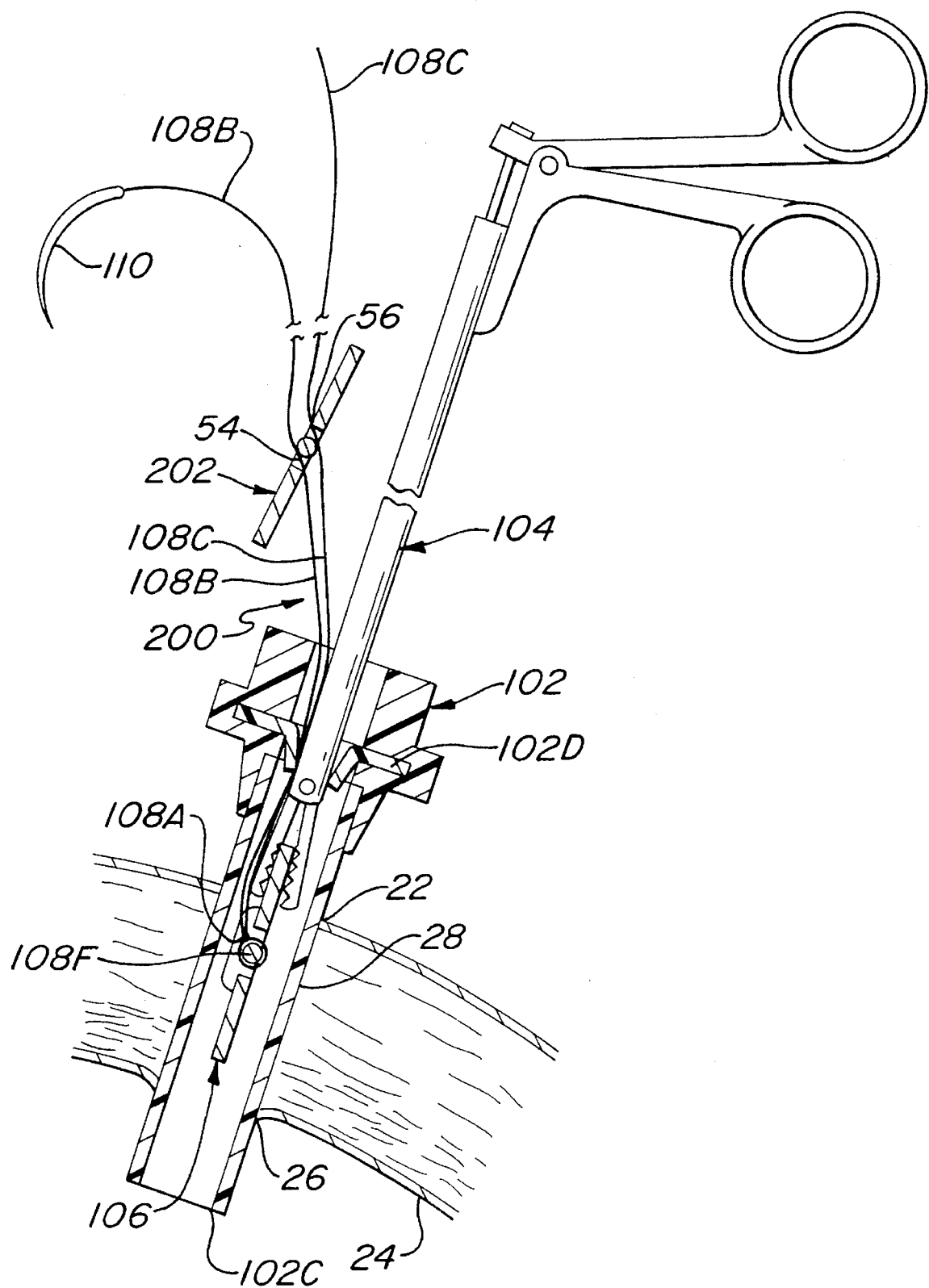
FIG. 23 is a side elevational view, like FIG. 15, but showing another alternative embodiment of a sealing device of this invention during the comparable step in the placement thereof as the device shown in FIG. 14.

In lieu of suturing the filament(s) to the skin and/or underlying tissue, other securement or fixing means can be used. In fact, it is contemplated that the securement of the free end(s) of the filament 108 be accomplished by a fixing member (to be described later) within the puncture tract itself, either remote from or in contact with the outer surface of the peritoneum, i.e., the surface opposite that which the anchoring member engages. In FIG. 23 there is shown an alternative embodiment for achieving that end. The alternative embodiment is denoted by the reference numeral 200 and is identical to the embodiment 100 except for two features, namely, the use of the fixing member mentioned above, and the inclusion of pair of filament ends (to be described later) extending from the anchoring member 106.

The method of using (deploying) the sealing device 200 is identical in most respects to the method of using the sealing device 100. Thus, in the interests of brevity the common components of devices 100 and 200 will be given the same reference numerals, and their structure and function will not be reiterated herein. Moreover, the complete method of using the sealing device 200 will not be discussed in detail, and only those steps which differ from those described earlier with reference to the sealing device 100 will be discussed in detail.

To that end, as can be seen the sealing device 200 includes the heretofore identified anchoring member 106 and the filament 108. The filament 108 includes a pair of end portions 108B and 108C which extend from the knot 108A affixing the filament to the hub 106F of the anchoring member 106. In addition the sealing device 200 includes the previously mentioned fixing member, identified by the reference numeral 202. The fixing member 202 is an elongated, substantially stiff member, which is preferably constructed similarly to the anchoring member 38 of the sealing device 20. The fixing member 202 includes a pair of apertures 54 and 56 through which the filament end portions 108B and 108C, respectively, extend. The free end of filament portion 108B includes the needle 110 mounted thereon.

The sealing of the percutaneous puncture tract into the abdomen using the sealing device 200 is accomplished as follows: with the trocar in place extending through the puncture so that its distal end 102C is within the abdomen, the physician utilizes the grasper 104 to insert the anchoring member 106 into the interior of the sheath of the trocar as described earlier and as shown in FIG. 23. The proximal portion of the filament end 108B with the needle 110 thereon remains outside of the trocar, as does the free end of the filament portion 108C. At this time the fixing member 202 is located outside of the trocar, and threaded on the filament portions 108B and 108C between the free ends thereof and the trocar.

The anchoring member is then introduced into the abdomen and trapped against the interior of the peritoneum contiguous with the opening therein in the same manner as described heretofore. The trocar is then removed from the extending filament portions 108B and 108C, while tension is maintained on those filament portions to keep the anchoring member 106 in position extending across the opening 26 in the peritoneum 24, with its domed portion 106D within the peritoneum opening 26.

Figure 24:
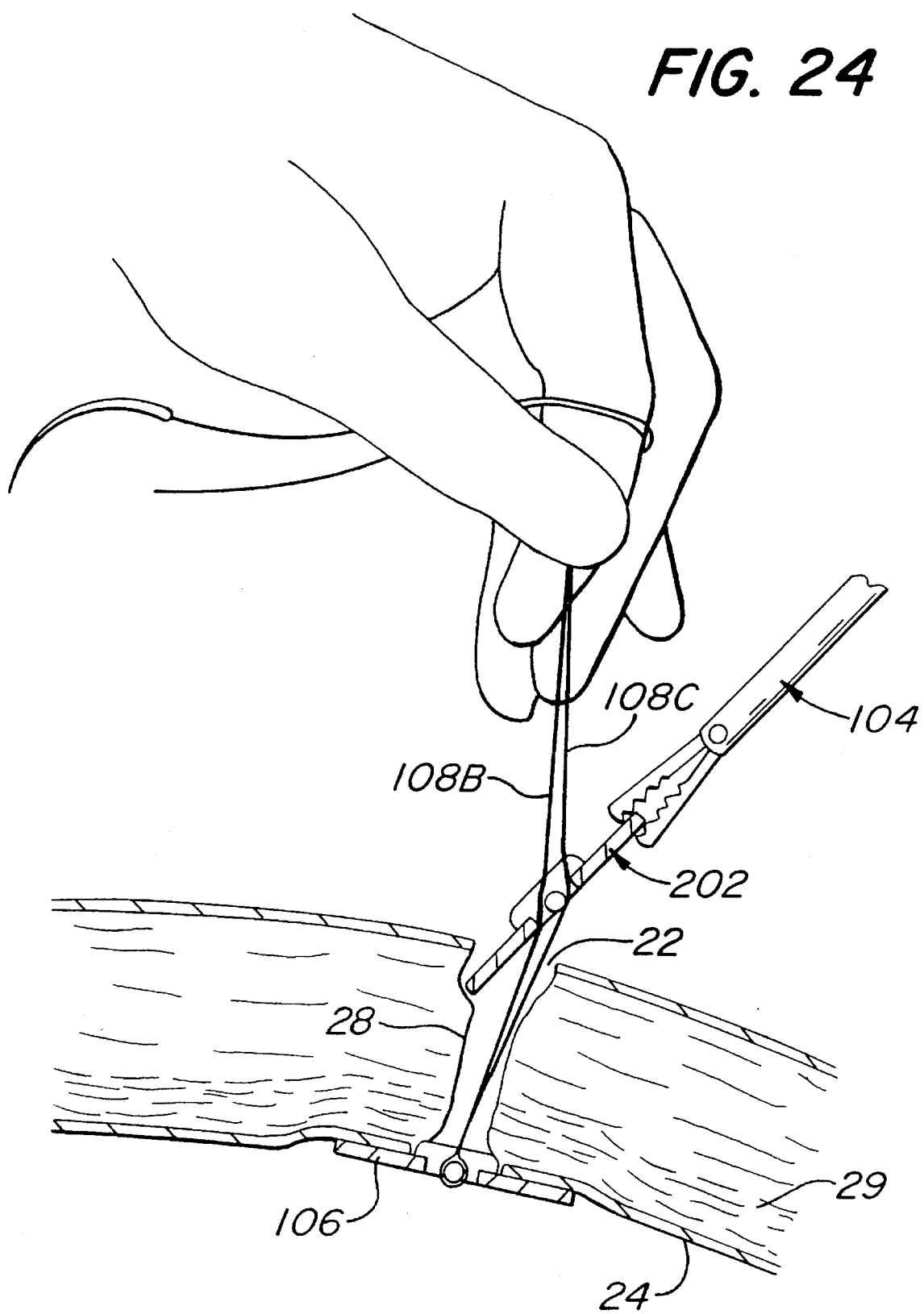
FIG. 24 is a side elevational view, like FIG. 20, but showing the location of a portion of the sealing device of FIG. 23 in place in the puncture tract to secure the device in place.

Then the grasper 104 is used to grasp one end of the fixing member 202 between its jaws 104A and 104B, and the grasped fixing member is slid down the filament portions 108B and 108C so that it enters into the puncture tract 28, while tension is maintained on at least one (and preferably both) of the filament portions 108B and 108C as shown in FIG. 24. This action ensures that the anchoring member 106 remains trapped against the interior of the peritoneum over opening 26. When the fixing member 202 is in a desired location within the puncture tract, e.g., at the interface 29 between the fatty fascia and muscle, the grasper 104 is manipulated to orient the fixing member so that the longitudinal axis of the fixing member is transverse to the longitudinal axis of the puncture tract.

Figure 25:
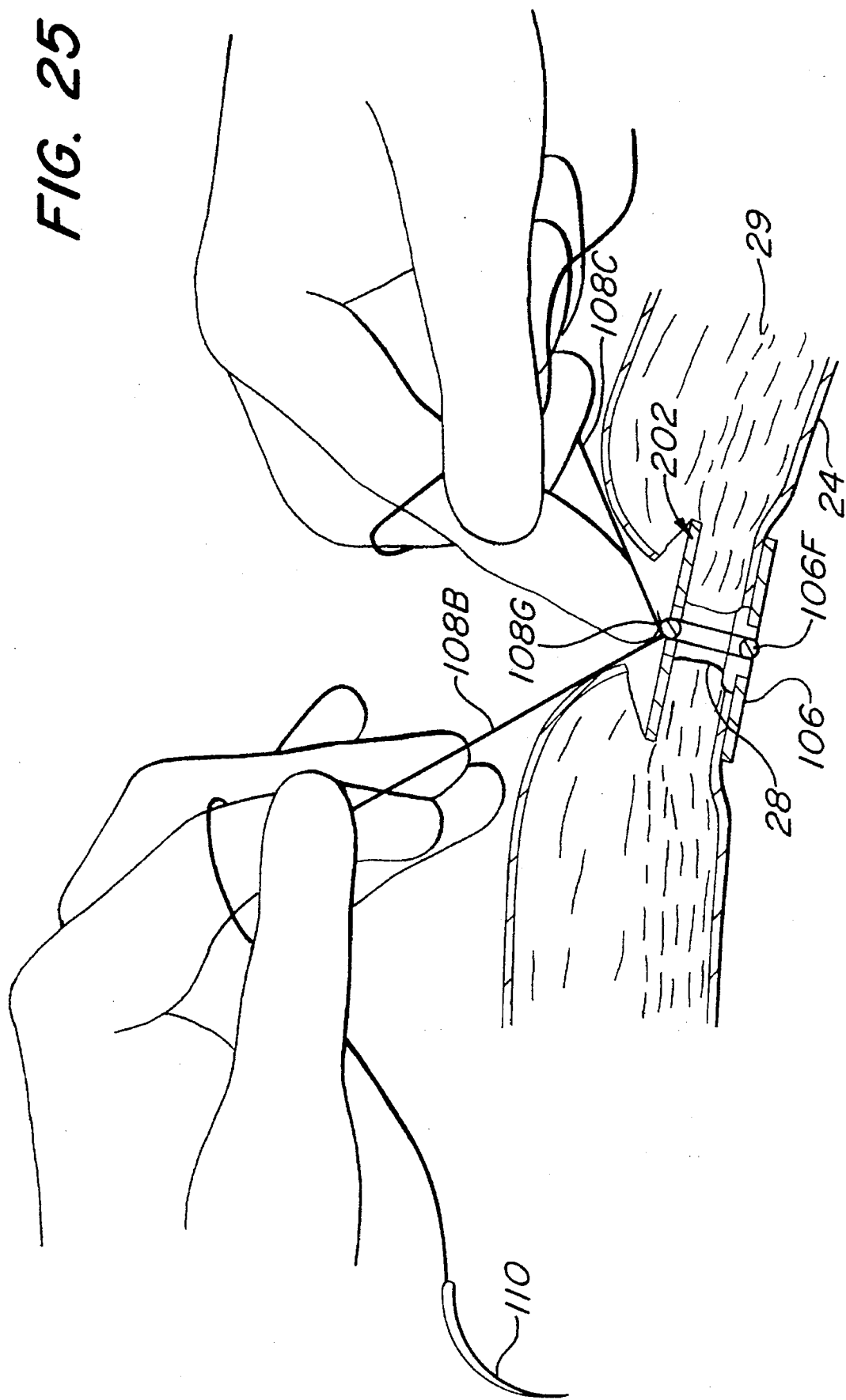
FIG. 25 is a side elevational, like that of FIG. 24, showing the sealing device of FIG. 23 being locked in place to fully install it within the percutaneous puncture.

The grasper 104 is then operated to release the fixing member from its jaws, and to retract the grasper out of the puncture tract. Once this is accomplished the two end portions 108B and 108C of the filament 108, which are still under tension, are knotted together at 108G immediately proximally of the fixing member 202 as shown in FIG. 25. This action keeps the portions of the filament 108 between the anchoring member 106 and the locking member 202 in tension, with the anchoring member trapped on the inner surface of the peritoneum and closing the opening 26 therein, thereby securing the sealing device 200 in place. The needle 110 on the free end of the filament portion 108B can then be used to suture the puncture tract together using the filament portion 108B contiguous with the skin, or below the skin, depending upon the desires of the surgeon. This action effectively closes the puncture tract. Once that has been accomplished the needle 110 may be removed, as described earlier.

As will be appreciated by those skilled in the art the timing of the resorption of the resorbable components of the sealing devices 20, 100 and 200 can be controlled by various means, e.g., the higher the molecular weight of the resorbable polymer, the longer the material will take to resorb. For example, if the anchoring members 20 or 106 (or any other resorbable portions of the devices 20, 100 and 200) are formed of a 100% polyglocolide resorbable polymer, as mentioned above, such components will have a longer resorption time than those of the 50—50 polylactide-co-glycolide mix, but should be more thermally stable during shipping.

It should be pointed out at this juncture that the sealing devices of the subject invention are not limited to protecting against the formation of a hernia at the site of a percutaneous puncture, but can be used to repair an existing hernia, as well. To that end the existing hernia can be penetrated from the outside by means of any suitable piercing instrument, e.g., a conventional or non-conventional trocar, to form a percutaneous puncture through the herniated tissue. Once this has been accomplished the devices of the subject invention can be inserted into the percutaneous puncture in the same manner as described earlier.

In order to facilitate the securing of the sealing devices 20, 100, and 200 in place within the percutaneous puncture, the anchoring member of the particular device may include elements on its top surface, i.e., the surface which engages the tissue. For example, the anchoring member may include spikes, treads, or other projections on its top surface to engage the inner surface of the tissue having the opening being sealed, e.g., the peritoneum, to aid in securing the anchor in place and to hold the edges of the opening contiguous with each other.

As mentioned earlier the sealing devices of the subject invention can be used to seal or close other percutaneous openings in internally located tissue, not only openings in the peritoneum, and to prevent the egress of tissue through the opening. For example, the devices of the subject invention can be used to close an opening in the wall of the thoracic cavity or lung, a herniated opening in the diaphragm, etc. Further still, and depending upon the application to which the invention is to be put, the anchoring member can be used to deliver a medication or a biologically acting material, e.g., an anti-adhesion drug may be coated on the anchoring member, an antibiotic or growth factor may be included in the anchoring member or coated thereon. Moreover, the anchoring member may be made radio-opaque to facilitate its placement or location, and may be formed of a single or multi-components.

Figure 26:
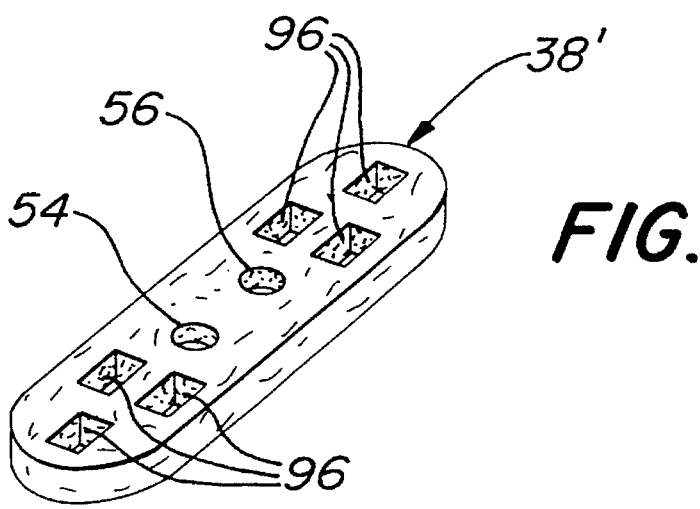
FIG. 26 is an elevational view of an alternative embodiment of an anchoring member which can be used in any of the sealing devices of this invention.
Figure 27:
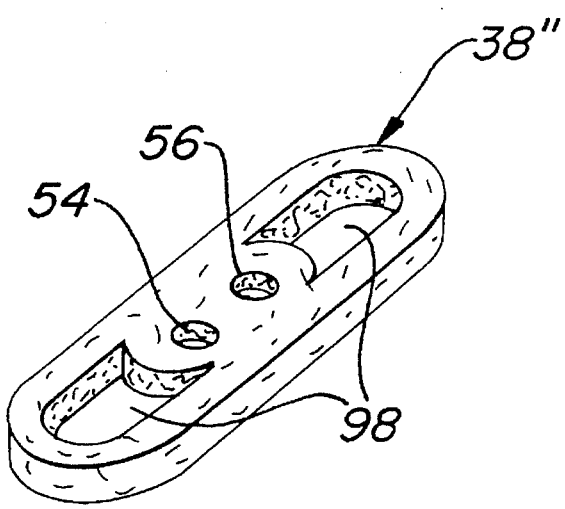
FIG. 27 is an elevational view, like that of FIG. 26, showing yet another alternative embodiment of an anchoring member which can be used in any of the sealing devices of this invention.
Figure 28:
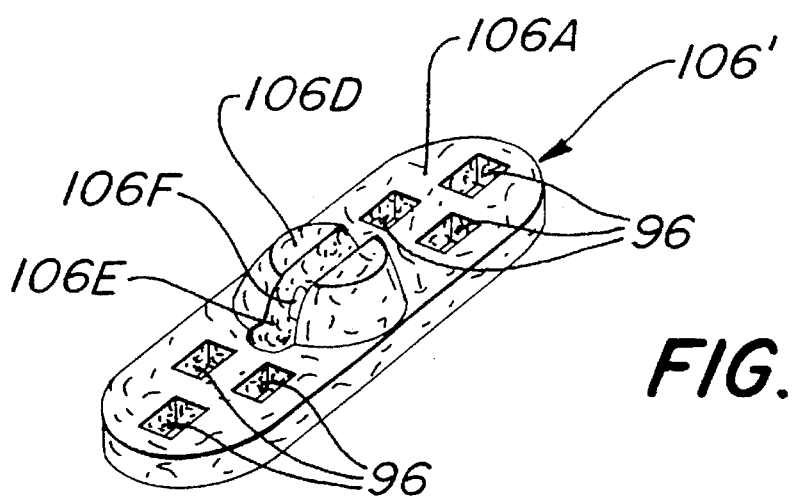
FIG. 28 is an elevational view, like that of FIGS. 26 and 27, showing still another alternative embodiment of an anchoring member which can be used in any of the sealing devices of this invention.

In FIGS. 26–28 there are shown alternative embodiments of anchoring members for the sealing devices of this invention. The anchoring members of these figures all share a common feature, namely, the inclusion of one or more apertures or holes extending transversely through the plane of the anchoring member, i.e., between its top surface and its bottom surface. These apertures or holes form voids into which tissue may grow when the anchoring member is in place as described earlier, thereby facilitating the securement of the sealing device in place. In particular, fibroblast intrusions into the voids in the anchoring member should more readily tend to engage the anchoring member securely to the tissue at the puncture site until the puncture heals. Another advantage of the use of apertures or voids in an anchoring member is a reduction in the resorption time of the member.

In FIGS. 26 and 27 there are shown alternative embodiments 38' and 38" respectively, of the anchoring member 38 described heretofore. The only differences in the construction of member 38' and 38" from the member 38 is the inclusion of a plurality of apertures or holes therein. Thus, in the interests of brevity the common features of the anchoring members 38, 38' and 38" will be given the same reference numbers and their construction and operation will not be reiterated. As can be seen in FIG. 26 the anchoring member 38' includes a plurality of apertures 96 extending through the body of the anchoring member from its top surface to its bottom surface. In the embodiment shown these apertures are square in shape, but that construction is merely exemplary. Thus, other shaped apertures, e.g., round, triangular, irregularly shaped, can be utilized. Moreover, the number of apertures incorporated into the anchoring member can be selected as desired. In this regard in FIG. 27 there is shown the anchoring embodiment 38" which includes only two apertures or holes 98 extending through the body of the anchoring member from its top surface to its bottom surface. The apertures 98 are large, and each is of irregular shape generally corresponding to the periphery of the anchoring member.

For applications wherein it is desired that a portion of the anchoring member enter and fill the opening in the tissue to be sealed, while enhancing the opportunity for tissue ingrowth into the anchoring member, the anchoring member may be constructed like the embodiment 106' shown in FIG. 28. Thus, the embodiment 106' constitutes an alternative to the embodiment 106 described above. The only difference in the construction of anchoring member 106' from the member 106 is the inclusion of a pair of apertures or holes 96 therein. Thus, the common features of the anchoring members 106 and 106' will be given the same reference numbers, and their construction and operation will not be reiterated. To that end as can be seen in FIG. 28 the apertures 96 in anchoring member 106' are constructed like those described above, but may be of alternative shape, size, and number, as also described above, e.g., may be like apertures 98.

It should be pointed out at this juncture that the apertures to create the tissue ingrowth voids in the anchoring members of this invention need not extend fully through the anchoring member, like apertures 96 and 98, but may only extend partially into the body of the anchoring member, e.g., the voids may be in the form of recesses, grooves, slots, cavities, etc., or other shapes, undercut or otherwise, forming space(s) into which the tissue at the puncture site may grow. Further, while the anchoring member and filament shown and described heretofore are described as being separate components which are secured together, it should be apparent that they may be formed as a unitary member, e.g., molded as a unit of a resorbable material like described above. In fact the needle may be molded integrally with the filament and anchoring member.

As mentioned earlier the anchoring member 106 (and for that matter member 106') includes a slot 106E in the dome portion thereof. This slot provides a passageway through which liquids or gasses may flow when the anchoring member is in place. For example, the slot may be utilized to enable the passage of $CO_2$ from the abdominal cavity out of the body, thereby helping to avoid trapping gas in the patient after the laparoscopic procedure is over. If it is desired to ensure that no gas or fluid passageway be provided, the central portion of anchoring which covers or fills the opening in the tissue may be unapertured, e.g., the slot eliminated, or constructed so that it does not extend from the top to the bottom of the anchoring member. Alternatively, the slot may be made sufficiently small that it is fully filled by the filament portion extending therein and about the hub 106F so that gas remains trapped within the patient. For applications to seal a percutaneous puncture in the thoracic cavity the anchoring means is preferably constructed in any of these alternative manners so that there is not passageway through which air can leak in to the thoracic cavity from the ambient surroundings through the anchoring member.

Without further elaboration the foregoing will so fully illustrate our invention that others may, by applying current or future knowledge, adopt the same for use under various conditions of service.

What is claimed is:

1. A device arranged for introduction through a percutaneous puncture into the body of a living being formed during a minimally invasive surgical procedure to prevent the egress of tissue into the puncture, the puncture comprising an opening in internal tissue in the body of the being and a tract extending from the skin of the being to the opening in the tissue, said device comprising anchoring means, filament means, and suturing means, said anchoring means being an elongated substantially rigid member arranged to be extended through the tract and the opening and being orientable for engaging the interior of the tissue adjacent the opening to render said anchoring means resistant to passage back through the opening, said filament means including a first portion and a second portion, said first portion extending between said anchoring means and said second portion and being coupled to said anchoring means for location within the tract, said second portion of said filament means extending out of the tract, said suturing means being coupled to said second portion of said filament means and being operative to cause said second portion of said filament means to penetrate tissue contiguous with the tract for holding said anchoring means permanently in place with respect to the puncture, with said anchoring means blocking at least a portion of the opening to prevent tissue from gaining egress into the puncture.

2. The device of claim 1 wherein said suturing means is releasably secured to said second portion of said filament means.

3. The device of claim 1 wherein said anchoring means additionally comprises a projecting portion for disposition within the opening when the device is in place.

4. The device of claim 1 wherein said anchoring means is formed of a resorbable material.

5. The device of claim 1 wherein said anchoring means includes reinforcing means formed of a reinforcing material, whereupon scar tissue forming at the opening is reinforced by said reinforcing material to prevent the herniation of said tissue.

6. The device of claim 1 additionally comprising an elongated member arranged for location and securement within the puncture tract.

7. The device of claim 1 wherein said device includes at least a portion which is radio-opaque.

8. The device of claim 1 wherein said device includes a biologically active material.

9. The device of claim 1 wherein said anchoring means includes means enabling tissue ingrowth into at least a portion of said anchoring means.

10. The device of claim 9 wherein said last mentioned means comprises plural perforations in said anchoring means.

11. A system for introduction through a percutaneous puncture into the body of a living being formed during a minimally invasive surgical procedure, the puncture comprising an opening in internal tissue in the body of the being and a tract extending from the skin of the being through the fascia to the opening, said system comprising a deployment instrument and an implantable device, said device comprising anchoring means, filament means, and suturing means, said anchoring means comprising an elongated substantially rigid member arranged to be extended by said instrument through the tract and the opening and being orientable for engaging the interior of the peritoneum adjacent the opening to render said anchoring means resistant to passage back through the opening, said filament means including a first portion and a second portion, said first portion extending between said anchoring means and said second portion and being coupled to said anchoring means for location with the tract, said second portion of said filament means extending out of the tract, said suturing means being coupled to said second portion of said filament means and being operative to cause said second portion of said filament means to penetrate tissue contiguous with the tract for holding said anchoring means permanently in place with respect to the puncture, with said anchoring means blocking at least a portion of the opening to prevent tissue from gaining egress through the puncture.

12. The system of claim 11 wherein said suturing means is releasably secured to said first portion of said filament means.

13. The system of claim 11 wherein said anchoring means additionally comprises a projecting portion for disposition within the opening when the device is in place.

14. The system of claim 11 wherein said anchoring means is formed of a resorbable material.

15. The system of claim 11 wherein said anchoring means includes reinforcing means formed of a reinforcing material, whereupon scar tissue forming at the opening is reinforced by said reinforcing material to prevent the herniation of said tissue.

16. The system of claim 11 wherein said device additionally comprises an elongated member arranged for location and securement within the puncture tract.

17. The system of claim 11 wherein said device includes at least a portion which is radio-opaque.

18. The system of claim 11 wherein said device includes a biologically active material.

19. The system of claim 11 wherein said anchoring means includes means enabling tissue ingrowth into at least a portion of said anchoring means.

20. The system of claim 11 wherein said last mentioned means comprises plural perforations in said anchoring means.

21. A device arranged for introduction through a percutaneous puncture into the body of a living being formed during a minimally invasive surgical procedure to prevent the ingress or egress of fluid through the puncture, the puncture comprising an opening in internal tissue in the body of the being and a tract extending from the skin of the being to the opening, said device comprising anchoring means, filament means, and suturing means, said anchoring means being an elongated substantially rigid member arranged to be extended through the tract and the opening and being orientable for engaging the interior of the tissue adjacent the opening to render said anchoring means resistant to passage back through the opening, said filament means including a first portion and a second portion, said first portion extending between said anchoring means and said second portion and being coupled to said anchoring means for location within the tract, said second portion of said filament means extending out of the tract, said suturing means being coupled to said second portion of said filament means and being operative to cause said second portion of said filament means to penetrate tissue contiguous with the tract for holding said anchoring means permanently in place with respect to the puncture, with said anchoring means blocking the opening to prevent fluid from flowing through the opening.

22. The device of claim 21 wherein said suturing means is releasably secured to said first portion of said filament means.

23. The device of claim 21 wherein said anchoring means additionally comprises a projecting portion for disposition within the opening when the device is in place.

24. The device of claim 21 wherein said anchoring means is formed of a resorbable material.

25. The device of claim 21 wherein said anchoring means includes reinforcing means formed of a reinforcing material.

26. The device of claim 21 additionally comprising an elongated member arranged for location and securement within the puncture tract.

27. The device of claim 21 wherein said device includes at least a portion which is radio-opaque.

28. The device of claim 21 wherein said device includes a biologically active material.

29. The device of claim 21 wherein said anchoring means includes means enabling tissue ingrowth into at least a portion of said anchoring means.

30. The device of claim 21 wherein said last mentioned means comprises plural perforations in said anchoring means.

31. A system for introduction through a percutaneous puncture into the body of a living being formed during a minimally invasive surgical procedure, the puncture comprising an opening in internal tissue in the body of the being and a tract extending from the skin of the being to the opening, said system comprising a deployment instrument and an implantable device, said device comprising anchoring means, filament means, and suturing means, said anchoring means comprising an elongated substantially rigid member arranged to be extended by said instrument through the tract and the opening and being orientable for engaging the interior of the tissue adjacent the opening to render said anchoring means resistant to passage back through the opening, said filament means including a first portion and a second portion, said first portion extending between said anchoring means and said second portion and being coupled to said anchoring means for location within the tract, said second portion of said filament means extending out of the tract, said suturing means being coupled to said second portion of said filament means and being operative to cause said second portion of said filament means to penetrate tissue contiguous with the tract for holding said anchoring means permanently in place with respect to the puncture, with said anchoring means blocking at least a portion of the opening to the flow of fluid therethrough.

32. The system of claim 31 wherein said suturing means is releasably secured to said first portion of said filament means.

33. The system of claim 31 wherein said anchoring means additionally comprises a projecting portion for disposition within the opening when the device is in place.

34. The system of claim 31 wherein said anchoring means is formed of a resorbable material.

35. The system of claim 31 wherein said anchoring means includes reinforcing means formed of a reinforcing material.

36. The system of claim 31 wherein said additionally comprises an elongated member arranged for location and securement within the puncture tract.

37. The system of claim 31 wherein said device includes at least a portion which is radio-opaque.

38. The system of claim 31 wherein said device includes a biologically active material.

39. The system of claim 31 wherein said anchoring means includes means enabling tissue ingrowth into at least a portion of said anchoring means.

40. The system of claim 39 wherein said last mentioned means comprises plural perforations in said anchoring means.

41. A method of preventing the egress of tissue into a percutaneous puncture formed during a minimally invasive surgical procedure on the body of a living being, said puncture having an opening in internal tissue in the body of the being and a tract extending from the skin of the being to the opening, said method comprising:

(a) providing a sealing device comprising anchoring means and filament means, said filament means being coupled to said anchoring means and including at least a first portion, (b) introducing said device through the puncture from the outside of the being's body and orienting said anchoring means so that said anchoring means engages the interior of the tissue adjacent the opening to render said anchoring means resistant to passage back through the opening, and (c) causing said first portion of said filament means to extend through the tract and securing said first portion of said filament means in place with respect to the tract for holding said anchoring means in place within the puncture, whereupon said anchoring means serves to block at least a portion of the opening to prevent the egress of tissue into the puncture.

42. The method of claim 41 wherein said internal tissue comprises the peritoneum.

43. The method of claim 42 wherein said method reduces the risk of the formation of a hernia at said opening.

44. The method of claim 43 wherein said anchoring means when in position serves to improve the long-term strength of scar tissue forming at the opening.

45. The method of claim 44 wherein said improvement of long-term strength of said scar tissue is accomplished by providing reinforcing means with said anchor, said reinforcing means being formed of a reinforcing material.

46. The method of claim 41 wherein said anchoring means when in position serves to improve the long-term strength of scar tissue forming at the opening.

47. The method of claim 46 wherein said improvement of long-term strength of said scar tissue is accomplished by providing reinforcing means with said anchor, said reinforcing means being formed of a reinforcing material.

48. The method of claim 41 additionally comprising securing said filament means to the skin of the being adjacent the tract to hold said device in place.

49. The method of claim 48 wherein said securement of said filament means to the skin is accomplished by suturing.

50. The method of claim 41 additionally comprising securing said filament means to tissue within the puncture tract to hold said device in place.

51. The method of claim 50 wherein said securement of said filament means to tissue within the puncture tract is accomplished by a fixing member located within the tract.

52. The method of claim 41 additionally comprising providing means to render said sealing device radio-opaque.

53. The method of claim 41 additionally comprising providing a biologically active agent carried by said sealing device.

54. The method of claim 41 additionally comprising promoting tissue ingrowth into said sealing device.

55. A method of sealing a percutaneous puncture extending into the body of a living being to prevent the flow of a fluid through the puncture, the percutaneous puncture having an opening in internal tissue within the body of the being and a tract extending from the skin of the being to the opening and being formed during a minimally invasive surgical procedure on the being, said method comprising:
  (a) providing a sealing device comprising anchoring means and filament means, said filament means being coupled to said anchoring means and including at least a first portion,
  (b) introducing said device through the puncture from the outside of being's body and orienting said anchoring means so that said anchoring means engages the interior of the tissue adjacent the opening to render said anchoring means resistant to passage back through the opening, and
  (c) causing said first portion of said filament means to extend through the tract securing said first portion of said filament means in place with respect to the tract for holding said anchoring means in place within the puncture, whereupon said anchoring means serves to block the opening to prevent the flow of fluid through the opening.

56. The method of claim 55 wherein said internal tissue comprises the wall of the thoracic cavity.

57. The method of claim 56 wherein said anchoring means when in position serves to improve the long-term strength of scar tissue forming at the opening.

58. The method of claim 57 wherein said improvement of long-term strength of said scar tissue is accomplished by providing reinforcing means with said anchor, said reinforcing means being formed of a reinforcing material.

59. The method of claim 55 wherein said anchoring means when in position serves to improve the long-term strength of scar tissue forming at the opening.

60. The method of claim 59 wherein said improvement of long-term strength of said scar tissue is accomplished by providing reinforcing means with said anchor, said reinforcing means being formed of a reinforcing material.

61. The method of claim 55 additionally comprising securing said filament means to the skin of the being adjacent the tract to hold said device in place.

62. The method of claim 61 wherein said securement of said filament means to the skin is accomplished by suturing.

63. The method of claim 55 additionally comprising securing said filament means to tissue within the puncture tract to hold said device in place.

64. The method of claim 63 wherein said securement of said filament means to tissue within the puncture tract is accomplished by a fixing member located within the tract.

65. The method of claim 55 additionally comprising providing means to render said sealing device radio-opaque.

66. The method of claim 55 additionally comprising providing a biologically active agent carried by said sealing device.

67. The method of claim 55 additionally comprising promoting tissue ingrowth into said sealing device.

68. A device arranged for introduction through a percutaneous puncture into the body of a living being formed during a minimally invasive surgical procedure to prevent egress of tissue into the puncture, the puncture comprising an opening in internal tissue in the body of the being and a tract extending from the skin of the being to the opening in the tissue, said device comprising anchoring means, filament means, suturing means, and retainer means, said anchoring means being an elongated substantially rigid member arranged to be extended through the tract and the opening and being orientable for engaging the interior of the tissue adjacent the opening to render said anchoring means resistant to passage back through the opening, said filament means including a first filament portion which is coupled to the anchoring means and the retainer means, and a second filament portion which passes at least partially along the remaining puncture tract to the skin, said suturing means being coupled to said second filament portion.

69. A device arranged for introduction through a percutaneous puncture into the body of a living being formed during a minimally invasive surgical procedure to prevent egress of tissue into the puncture, the puncture comprising an opening in internal tissue in the body of the being and a tract extending from the skin of the being to the opening in the tissue, said device comprising anchoring means, filament means, carrier means, and retainer means, said anchoring means being an elongated substantially rigid member arranged to be extended through the tract and the opening and being orientable for engaging the interior of the tissue adjacent the opening to render said anchoring means resistant to passage back through the opening, said filament means including a first filament portion which is coupled to the anchoring means and the retainer means, and a second filament portion which passes at least partially along the remaining puncture tract to the skin, said carrier means being a thin, relatively stiff member coupled to said second filament portion and arranged to be grasped for carrying said second filament portion to a position whereupon said second filament portion is permanently fixed with respect to the tract.

70. The device of claim 69 wherein said carrier means comprising a needle for penetrating tissue of the being adjacent the tract.

71. The device of claim 70 wherein said needle is releasably secured to said second filament portion.

72. A device arranged for introduction through a percutaneous puncture into the body of a living being formed during a minimally invasive surgical procedure for preventing the ingress or egress of fluid through the puncture, the puncture comprising an opening in internal tissue in the body of the being and a tract extending from the skin of the being to the opening in the tissue, said device comprising anchoring means, filament means, suturing means, and retainer means, said anchoring means being an elongated substantially rigid member arranged to be extended through the tract and the opening and being orientable for engaging the interior of the tissue adjacent the opening to render said anchoring means resistant to passage back through the opening, said filament means including a first filament portion which is coupled to the anchoring means and the retainer means, and a second filament portion which passes at least partially along the remaining puncture tract to the skin, said suturing means being coupled to said second filament portion.

73. A device arranged for introduction through a percutaneous puncture into the body of a living being formed during a minimally invasive surgical procedure for preventing the ingress or egress of fluid through the puncture, the puncture comprising an opening in internal tissue in the body of the being and a tract extending from the skin of the being to the opening in the tissue, said device comprising anchoring means, filament means, carrier means, and retainer means, said anchoring means being an elongated substantially rigid member arranged to be extended through the tract and the opening and being orientable for engaging the interior of the tissue adjacent the opening to render said anchoring means resistant to passage back through the opening, said filament means including a first filament portion which is coupled to the anchoring means and the retainer means, and a second filament portion which passes at least partially along the remaining puncture tract to the skin, said carrier means being a thin, relatively stiff member coupled to said second filament portion and arranged to be grasped for carrying said second filament portion to a position whereupon said second filament portion is permanently fixed with respect to the tract.

74. The device of claim 73 wherein said carrier means comprising a needle for penetrating tissue of the being adjacent the tract.

75. The device of claim 74 wherein said needle is releasably secured to said second filament portion.

* * * * *

UNITED STATES PATENT AND TRADEMARK OFFICE
CERTIFICATE OF CORRECTION

PATENT NO. : 5,545,178
DATED : August 13, 1996
INVENTOR(S) : Kenneth Kensey, John E. Nash, Douglas Evans and Todd M. DeWitt It is certified that error appears in the above-identified patent and that said Letters Patent is hereby corrected as shown below:

On the title page: Item [75] after "Douglas Evans, Devon" delete the "," and insert therefore a -- ; -- and thereafter, insert the following: -- Todd M. DeWitt, Pottstown, --

Signed and Sealed this

Seventh Day of January, 1997

Attest:

BRUCE LEHMAN

Attesting Officer   Commissioner of Patents and Trademarks